(12) United States Patent
Chaudhuri et al.

(10) Patent No.: US 8,685,727 B2
(45) Date of Patent: Apr. 1, 2014

(54) REGULATION OF MACROPHAGE ACTIVATION USING MIR-125B

(75) Inventors: Aadel Chaudhuri, Santa Clara, CA (US); Alex Steven So, Los Angeles, CA (US); David Baltimore, Pasadena, CA (US); Ryan M. O'Connell, Salt Lake City, UT (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/526,347

(22) Filed: Jun. 18, 2012

(65) Prior Publication Data
US 2012/0322854 A1 Dec. 20, 2012

Related U.S. Application Data

(60) Provisional application No. 61/499,035, filed on Jun. 20, 2011, provisional application No. 61/527,081, filed on Aug. 24, 2011, provisional application No. 61/527,108, filed on Aug. 24, 2011.

(51) Int. Cl.
*C12N 15/85* (2006.01)
*C07H 21/02* (2006.01)
*C07H 21/04* (2006.01)

(52) U.S. Cl.
USPC .................. 435/325; 536/23.1; 536/24.5

(58) Field of Classification Search
None
See application file for complete search history.

(56) References Cited

U.S. PATENT DOCUMENTS

2005/0261218 A1  11/2005  Esau et al.
2008/0261908 A1  10/2008  Croce et al.

FOREIGN PATENT DOCUMENTS

WO   WO 2011/017030   2/2011

OTHER PUBLICATIONS

Androulidaki et al. The kinase Akt1 controls macrophage response to lipopolysaccharide by regulating microRNAs. Immunity, 31(2):220-231 (2009).
Baltimore et al. MicroRNAs: new regulators of immune cell development and function, Nat. Immunol. 9(8):839-845 ((2008).
Bazzoni et al., Induction and regulatory function of miR-9 in human monocytes and neutrophils exposed to proinflammatory signals. Proc. Natl. Acad. Sci. USA, 106(13):5282-5287 (2009).
Bousquet et al., Myeloid cell differentiation arrest by miR-125b-1 in myelodysplastic syndrome and acute myeloid leukemia with the t(2;11)(p21;q23) translocation. The Journal of experimental medicine, 205(11):2499-2506 (2008).
Bousquet et al., MicroRNA miR-125b causes leukemia. Proc. Natl. Acad. Sci. USA, 107(50):21558-21563 (2010).
Chaudhuri et al., MicroRNA-125b potentiates macrophage activation. J. Immunol., 187(10):5062-5068 (2011).
Davis et al., Potent inhibition of microRNA in vivo without degradation. Nucleic Acids Res., 37(1):70-77 (2009).
Dideberg et al., An insertion-deletion polymorphism in the interferon regulatory Factor 5 (IRF5) gene confers risk of inflammatory bowel diseases. Hum. Mol. Genet., 16(24):3008-3016 (2007).
Friedman et al., Most mammalian mRNAs are conserved targets of microRNAs. Genome Res., 19(1):92-105 (2009).
Gefen et al., Hsa-mir-125b-2 is highly expressed in childhood ETV6/RUNX1 (TEL/AML1) leukemias and confers survival advantage to growth inhibitory signals independent of p53. Leukemia, 24(1):89-96 (2010).
Glud et al., Downregulation of miR-125b in metastatic cutaneous malignant melanoma. Melanoma Research, 20(6):479-484 (2010).
Graham et al., A common haplotype of interferon regulatory factor 5 (IRF5) regulates splicing and expression and is associated with increased risk of systemic lupus erythematosus. Nat. Genet., 38(5):550-555 (2006).
Graham et al. Three functional variants of IFN regulatory factor 5 (IRF5) define risk and protective haplotypes for human lupus. Proc. Natl. Acad. Sci. USA, 104(16):6758-6763 (2007).
Grimson et al., MicroRNA targeting specificity in mammals: determinants beyond seed pairing. Mol Cell, 27(1):91-105 (2007).
Griffiths-Jones et al., miRBase: microRNA sequences, targets and gene nomenclature. Nucleic acids Research, 34(Database issue):D140-144 (2006).
Griffiths-Jones et al., miRBase: tools for microRNA genomics. Nucleic acids research, 36(Database issue):D154-158 (2008).
Guan et al., MiR-125b targets BCL3 and suppresses ovarian cancer proliferation. Int. J. Cancer, 128(10):2274-2283 (2011).
Gururajan et al. MicroRNA 125b inhibition of B cell differentiation in germinal centers. Int Immunol., 22(7):583-592 (2010).
Han et al., Association of polymorphisms in interferon regulatory factor 5 gene with rheumatoid arthritis: a metaanalysis. J. Rheumatol. 36(4):693-697 (2009).
He & Hannon, MicroRNAs: small RNAs with a big role in gene regulation. Nat. Rev. Genet., 5(7):522-531 (2004).
Henson et al., Decreased expression of miR-125b and miR-100 in oral cancer cells contributes to malignancy. Genes Chromosomes Cancer, 48(7):569-582 (2009).
Honma et al., Interferon regulatory factor 4 negatively regulates the production of proinflammatory cytokines by macrophages in response to LPS. Proc. Natl. Acad. Sci. USA, 102(44):16001-16006 (2005).

(Continued)

*Primary Examiner* — Amy Bowman
(74) *Attorney, Agent, or Firm* — Knobbe, Martens, Olson & Bear LLP

(57) ABSTRACT

The present disclosure relates to regulation of macrophage activation by delivering of miRNAs, for example miR-125b or anti-miR-125b, to macrophages. For example, in some embodiments, macrophage activation can be elevated or reduced by administering miR-125b or anti-miR-125b oligonucleotides. Also disclosed are methods for promoting T cell activation and method for treating various disorders such as tumor and autoimmune diseases.

16 Claims, 16 Drawing Sheets

(56) References Cited

OTHER PUBLICATIONS

Hoshi et al., Implications for differential diagnosis of lung cancer associated lymphadenopathy in lymphoepithelioid cell lymphoma (Lennert's lymphoma) arising simultaneously with lung cancer: a case report. Acta Cytol 54(2):197-201 (2010).
Klein et al., Transcription factor IRF4 controls plasma cell differentiation and class-switch recombination. Nat. Immunol., 7(7):773-782 (2006).
Klusmann et al., miR-125b-2 is a potential oncomiR on human chromosome 21 in megakaryoblastic leukemia. Genes & development, 24(5):478-490 (2010).
Krausgruber et al., IRF5 promotes inflammatory macrophage polarization and TH1-TH17 responses. Nat. Immunol., 12(3):231-238 (2011).
Kristjansdottir et al., Interferon regulatory factor 5 (IRF5) gene variants are associated with multiple sclerosis in three distinct populations. J. Med. Genet., 45(6):362-369 (2008).
Le et al., MicroRNA-125b is a novel negative regulator of p53. Genes Dev., 23(7):862-876 (2009).
Lewis et al., Conserved seed pairing, often flanked by adenosines, indicates that thousands of human genes are microRNA targets. Cell. 120(1):15-20 (2005).
Liu et al., miR-147, a microRNA that is induced upon Toll-like receptor stimulation, regulates murine macrophage inflammatory responses. Proc. Natl. Acad. Sci. USA, 106(37):15819-15824 (2009).
Iorio et al., MicroRNA gene expression deregulation in human breast cancer. Cancer research, 65(16):7065-7070 (2005).
Malumbres et al. Differentiation stage-specific expression of microRNAs in B lymphocytes and diffuse large B-cell lymphomas. Blood, 113(16):3754-3764 (2009).
Murphy et al., Estradiol suppresses NF-kappa B activation through coordinated regulation of let-7a and miR-125b in primary human macrophages. J. Immunol., 184(9):5029-5037 (2010).
Negishi et al. Negative regulation of Toll-like-receptor signaling by IRF-4. Proc. Natl. Acad. Sci. USA, 102(44):15989-15994 (2005).
O'Connell et al., MicroRNA-155 is induced during the macrophage inflammatory response. Proc. Natl. Acad. Sci. USA, 104(5):1604-1609 (2007).
O'Connell et al., Sustained expression of microRNA-155 in hematopoietic stem cells causes a myeloproliferative disorder. The Journal of experimental medicine, 205(3):585-594 (2008).
O'Connell et al., Inositol phosphatase SHIP1 is a primary target of miR-155. Proc. Natl. Acad. Sci. USA, 106(17):7113-7118 (2009).
O'Connell et al., MicroRNAs enriched in hematopoietic stem cells differentially regulate longterm hematopoietic output. Proc. Natl. Acad. Sci. USA. 107(32):14235-14240 (2010).
O'Connell et al., Physiological and pathological roles for microRNAs in the immune system. Nat. Rev. Immunol., 10(2):111-122 (2010).
Ooi et al., MicroRNA-125b expands hematopoietic stem cells and enriches for the lymphoid-balanced and lymphoid-biased subsets. Proc. Natl. Acad. Sci. USA., 107(50):21505-21510 (2010).
Ozen et al., Widespread deregulation of microRNA expression in human prostate cancer. Oncogene, 27(12):1788-1793 (2008).
Rao et al., MicroRNA-34a perturbs B lymphocyte development by repressing the forkhead box transcription factor Foxp1. Immunity, 33(1):48-59 (2010).
Sheedy et al., Negative regulation of TLR4 via targeting of the proinflammatory tumor suppressor PDCD4 by the microRNA miR-21. Nat. Immunol. 11(2):141-147 (2010).
Shi et al., An androgen-regulated miRNA suppresses Bak1 expression and induces androgen-independent growth of prostate cancer cells. Proc. Natl. Acad. Sci. USA, 104(50):19983-19988 (2007).
Shimane et al. A single nucleotide polymorphism in the IRF5 promoter region is associated with susceptibility to rheumatoid arthritis in the Japanese population. Ann. Rheum. Dis., 68(3):377-383 (2009).
Sigurdsson et al., Comprehensive evaluation of the genetic variants of interferon regulatory factor 5 (IRF5) reveals a novel 5 bp length polymorphism as strong risk factor for systemic lupus erythematosus. Hum. Mol. Genet., 17(6):872-881 (2008).
Solinas et al., Tumor associated macrophages (TAM) as major players of the cancer-related inflammation. J. Leukoc. Biol., 86(5):1065-1073 (2009).
Taganov KD, Boldin MP, Chang KJ, & Baltimore D (2006) NF-kappaB dependent induction of microRNA miR-146, an inhibitor targeted to signaling proteins of innate immune responses. Proc. Natl. Acad. Sci. USA, 103(33):12481-12486.
Tili et al., Modulation of miR-155 and miR-125b levels following lipopolysaccharide/TNF-alpha stimulation and their possible roles in regulating the response to endotoxin shock. J. Immunol., 179(8):5082-5089(2007).
Vandenbroeck et al., Validation of IRF5 as multiple sclerosis risk gene: putative role in interferon beta therapy and human herpes virus-6 infection. Genes Immun., 12(1):40-45 (2011).
Visone et al., Specific microRNAs are downregulated in human thyroid anaplastic carcinomas. Oncogene, 26(54):7590-7595 (2007).
Vosslamber et al., Interferon regulatory factor 5 gene variants and pharmacological and clinical outcome of Interferonbeta therapy in multiple sclerosis. Genes Immun. 12(6):466-472 (2011).
Wong et al., Mature miR-184 as potential oncogenic microRNA of squamous cell carcinoma of tongue. Clinical Cancer Research, 14(9):2588-2592 (2008).
Xia et al., MiR-125b expression affects the proliferation and apoptosis of human glioma cells by targeting Bmf. Cell Physiol. Biochem., 23(4-6):347-358 (2009).
Yanagimachi et al., Association of IRF5 polymorphisms with susceptibility to macrophage activation syndrome in patients with juvenile idiopathic arthritis. J. Rheumatol., 38(4):769-774 (2011).
Yang & Baltimore, Long-term in vivo provision of antigen-specific T cell immunity by programming hematopoietic stem cells. Proc. Natl. Acad. Sci. USA, 102(12):4518-4523 (2005).
Yang et al., MicroRNA expression profiling in human ovarian cancer: miR-214 induces cell survival and cisplatin resistance by targeting PTEN. Cancer Research, 68(2):425-433 (2008).
Zhou et al., Binding of NF-kappaB p65 subunit to the promoter elements is involved in LPS-induced transactivation of miRNA genes in human biliary epithelial cells. Nucleic acids research, 38(10):3222-3232 (2010).
International Search Report and Written Opinion dated Dec. 28, 2012 for international application PCT/US2012/043010, filed Jun. 8, 2012.
Lewis et al., Prediction of Mammalian MicroRNA Targets, Cell, 115:787-798 (2003).
Takane et al., Computational Prediction and Experimental Validation of Evolutionarily Conserved microRNA Target Genes in Bilaterian Animals. BMC Genomics, 11:101 (2010).
Thadani et al., MicroTar: Predicting microRNA Targets from RNA Duplexes, BMC Bioinformatics, 7(Suppl 5):S20 (2006).
Zhang et al., MicroRNA 125a and Its Regulation of the p53 Tumor Suppressor Gene, FEBS Letters 583:3735-3730 (2009).
ATCC deposit record for RAW 264.7 (ATCC® TIB-71™), retrieved on Nov. 19, 2013.

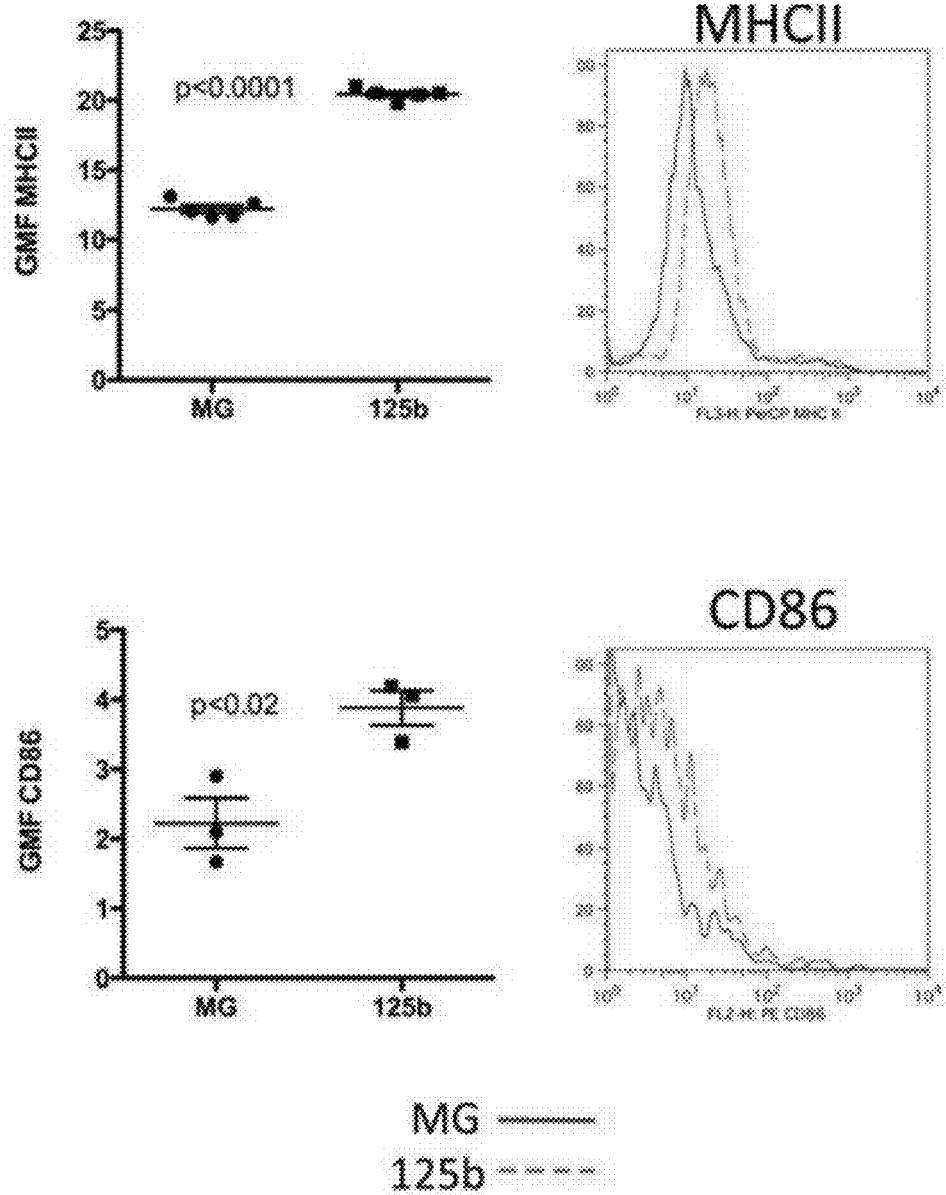

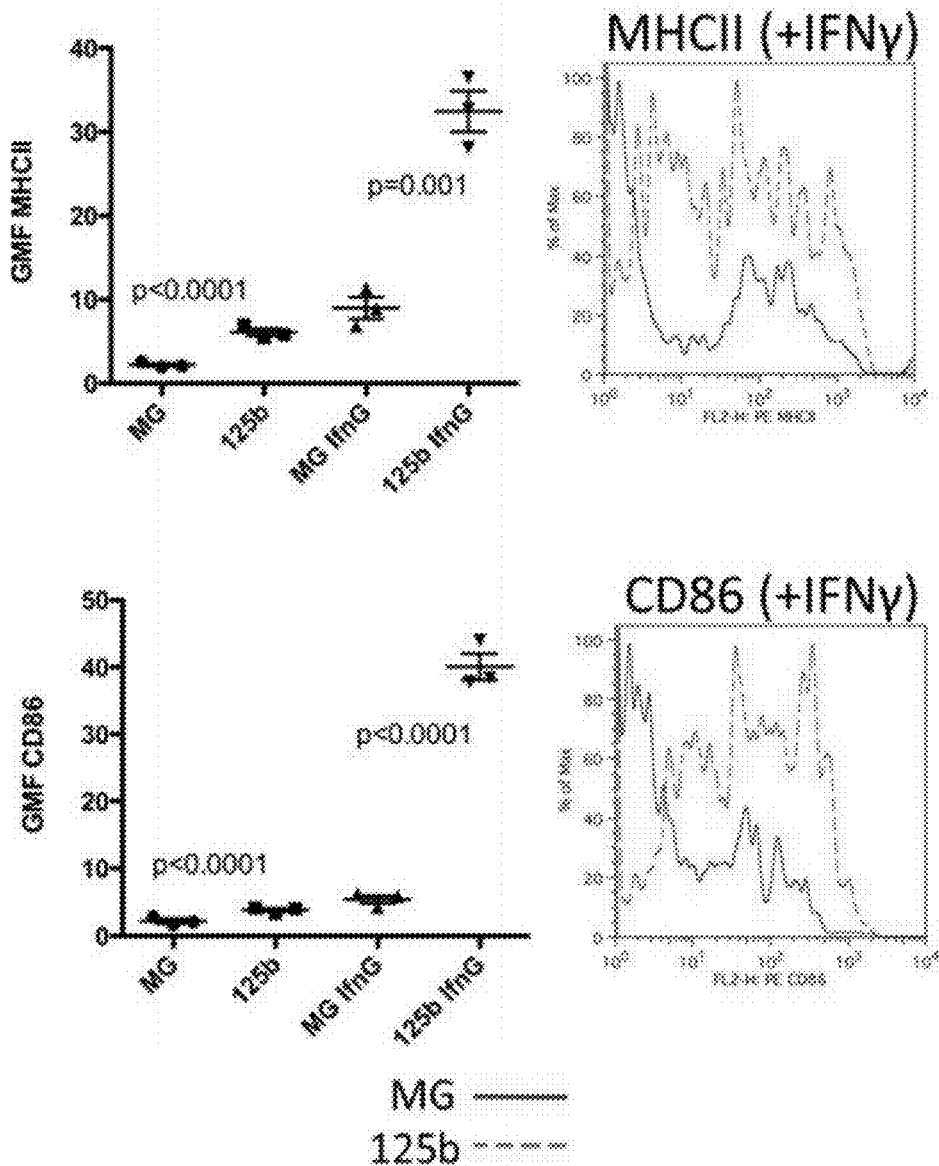

C.

D.

E.

```
SEQUENCE LISTING

<160> NUMBER OF SEQ ID NOS: 32

<210> SEQ ID NO 1
<211> LENGTH: 22
<212> TYPE: RNA
<213> ORGANISM: Homo sapiens

<400> SEQUENCE: 1
ucccugagac ccuaacuugu ga                                              22

<210> SEQ ID NO 2
<211> LENGTH: 88
<212> TYPE: RNA
<213> ORGANISM: Homo sapiens

<400> SEQUENCE: 2
ugcgcuccuc ucagucccug agacccuaac uugugauguu uaccguuuaa auccacgggu     60
uaggcucuug ggagcugcga gucgugcu                                        88

<210> SEQ ID NO 3
<211> LENGTH: 89
<212> TYPE: RNA
<213> ORGANISM: Homo sapiens

<400> SEQUENCE: 3
accagacuuu uccuaguccc ugagacccua acuugugagg uauuuuagua acaucacaag     60
ucaggcucuu gggaccuagg cggagggga                                       89

<210> SEQ ID NO 4
<211> LENGTH: 8
<212> TYPE: RNA
<213> ORGANISM: Homo sapiens

<400> SEQUENCE: 4 cccugaga                                                              8

<210> SEQ ID NO 5
<211> LENGTH: 22
<212> TYPE: RNA
<213> ORGANISM: Mus musculus

<400> SEQUENCE: 5
ucccugagac ccuaacuugu ga                                              22

<210> SEQ ID NO 6
<211> LENGTH: 77
<212> TYPE: RNA
```

-continued

<213> ORGANISM: Mus musculus

<400> SEQUENCE: 6
ugcgcucccc ucagucccug agacccuaac uugugauguu uaccguuuaa auccacgggu    60
uaggcucuug ggagcug                                                   77

<210> SEQ ID NO 7
<211> LENGTH: 8
<212> TYPE: RNA
<213> ORGANISM: Mus musculus

<400> SEQUENCE: 7 cccugaga                                                              8

<210> SEQ ID NO 8
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 8
agggacucug ggauugaaca cu                                             22

<210> SEQ ID NO 9
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 9
agggacucug ggauugaaca cu                                             22

<210> SEQ ID NO 10
<211> LENGTH: 88
<212> TYPE: RNA
<213> ORGANISM: Artificial Sequence
<220> FEATURE:
<223> OTHER INFORMATION: Synthetic oligonucleotide

<400> SEQUENCE: 10
acgcgaggag agucagggac ucugggauug aacacuacaa auggcaaauu uaggugccca    60
auccgagaac ccucgacgcu cagcacga                                       88

<210> SEQ ID NO 11
<211> LENGTH: 89
<212> TYPE: RNA
<213> ORGANISM: Artificial Sequence
<220> FEATURE:
<223> OTHER INFORMATION: Synthetic oligonucleotide

<400> SEQUENCE: 11
uggucugaaa aggaucaggg acucugggau ugaacacucc auaaaaucau uguaguguuc    60
aguccgagaa cccuggaucc gccucccu                                       89

<210> SEQ ID NO 12
<211> LENGTH: 77
<212> TYPE: RNA
<213> ORGANISM: Artificial Sequence
<220> FEATURE:
<223> OTHER INFORMATION: Synthetic oligonucleotide

<400> SEQUENCE: 12

-continued acgcgagggg agucagggac ucugggauug aacacuacaa auggcaaauu uaggugccca    60
auccgagaac ccucgac    77

<210> SEQ ID NO 13
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 13 gggacucu    8

<210> SEQ ID NO 14
<211> LENGTH: 8
<212> TYPE: RNA
<213> ORGANISM: Artificial Sequence
<220> FEATURE:
<223> OTHER INFORMATION: Synthetic oligonucleotide

<400> SEQUENCE: 14 gggacucu    8

<210> SEQ ID NO 15
<211> LENGTH: 22
<212> TYPE: RNA
<213> ORGANISM: Artificial Sequence
<220> FEATURE:
<223> OTHER INFORMATION: Synthetic nucleic acid

<400> SEQUENCE: 15
ucccugagac ccuaacuugu ga    22

<210> SEQ ID NO 16
<211> LENGTH: 50
<212> TYPE: RNA
<213> ORGANISM: Homo sapiens

<400> SEQUENCE: 16
gcuuguaggu augucugugc cauuucucag ggaaguaaga uguaaauuga    50

<210> SEQ ID NO 17
<211> LENGTH: 50
<212> TYPE: RNA
<213> ORGANISM: Mus musculus

<400> SEQUENCE: 17
agacauacgu auuauugguc cauuucucag ggaaguaaag ucuagacuag    50

<210> SEQ ID NO 18
<211> LENGTH: 50
<212> TYPE: RNA
<213> ORGANISM: Felis catus

<400> SEQUENCE: 18
aaguacuuua agugcuguac uauuucucag ggaaguaaua ucuaaauuug    50

<210> SEQ ID NO 19
<211> LENGTH: 46
<212> TYPE: RNA
<213> ORGANISM: Dasypus novemcinctus

<400> SEQUENCE: 19
cacuuaggug uuguaccauu ucucagggaa guaaaaucga ggcuac    46

<210> SEQ ID NO 20
<211> LENGTH: 90
<212> TYPE: DNA
<213> ORGANISM: Artificial Sequence
<220> FEATURE:
<223> OTHER INFORMATION: IRF4 shRNA oligo

<400> SEQUENCE: 20
gaaggctgta tgctgaaaca atgcccaagc cttgaagttt tggccactga ctgacttcaa      60
ggcgggcatt gtttcaggac acaaggcctg                                       90

<210> SEQ ID NO 21
<211> LENGTH: 43
<212> TYPE: DNA
<213> ORGANISM: Artificial Sequence
<220> FEATURE:
<223> OTHER INFORMATION: IRF4 3' UTR NOTI FW

<400> SEQUENCE: 21
ttcgcggccg cgagtttttct ctgatgtact cgtgatcgta tgt                       43

<210> SEQ ID NO 22
<211> LENGTH: 34
<212> TYPE: DNA
<213> ORGANISM: Artificial Sequence
<220> FEATURE:
<223> OTHER INFORMATION: IRF4 3' UTR XHOI REV

<400> SEQUENCE: 22
ttcctcgaga acagaaatcc aggagctgcc actc                                  34

<210> SEQ ID NO 23
<211> LENGTH: 50
<212> TYPE: DNA
<213> ORGANISM: Artificial Sequence
<220> FEATURE:
<223> OTHER INFORMATION: 2MER SPEI FW

<400> SEQUENCE: 23
ctagttcaca agttagggtc tcagggatca caagttaggg tctcagggaa                 50

<210> SEQ ID NO 24
<211> LENGTH: 50
<212> TYPE: DNA
<213> ORGANISM: Artificial Sequence
<220> FEATURE:
<223> OTHER INFORMATION: 2MER HINDIII REV

<400> SEQUENCE: 24
agctttccct gagaccctaa cttgtgatcc ctgagaccct aacttgtgaa                 50

<210> SEQ ID NO 25
<211> LENGTH: 20
<212> TYPE: DNA
<213> ORGANISM: Artificial Sequence
<220> FEATURE:
<223> OTHER INFORMATION: IRF4 QPCR FW

<400> SEQUENCE: 25
tccgacagtg gttgatcgac                                                  20

<210> SEQ ID NO 26
<211> LENGTH: 22
<212> TYPE: DNA
<213> ORGANISM: Artificial Sequence
<220> FEATURE:

<223> OTHER INFORMATION: IRF4 QPCR REV

<400> SEQUENCE: 26
cctcacgatt gtagtcctgc tt                                           22

<210> SEQ ID NO 27
<211> LENGTH: 19
<212> TYPE: DNA
<213> ORGANISM: Artificial Sequence
<220> FEATURE:
<223> OTHER INFORMATION: L32 QPCR FW

<400> SEQUENCE: 27
aagcgaaact ggcggaaac                                               19

<210> SEQ ID NO 28
<211> LENGTH: 20
<212> TYPE: DNA
<213> ORGANISM: Artificial Sequence
<220> FEATURE:
<223> OTHER INFORMATION: L32 QPCR REV

<400> SEQUENCE: 28
taaccgatgt tgggcatcag                                              20

<210> SEQ ID NO 29
<211> LENGTH: 480
<212> TYPE: DNA
<213> ORGANISM: Homo sapiens

<400> SEQUENCE: 29
gagttttctc tgatgtactc gtgatcgtat gtgtatgtgc gtgattgtat atgcgcccccc    60
agatactgcg tatgtgtgta tatatgtatt aggcttaaac ggaatctcaa ttttgtgaag   120
gaaaggagct tagagaagaa ataccatacc acctgtttgt tgcatcttag ttatgaacct   180
cgaacagaaa ttgcctgtca ttcttgtttt gctttgcttt gtctcaagaa agaaaacatt   240
gttgcgctcc tctcagtccc tgagacccta acttgtgatg tttaccgttt aaatccacgg   300
gttaggctct gggagctgc gagtcgtgct tttgcatcct ggaaatttgg tggaattttta   360
ttctttaaag caaaaacaaa agaaaagaaa gtttgtctga ggtgattgag tatacctctg   420
aggttttcat tgttagatgg gatcaggtga ccagagagtg gcagctcctg gatttctgtt   480

<210> SEQ ID NO 30
<211> LENGTH: 522
<212> TYPE: DNA
<213> ORGANISM: Homo sapiens

<400> SEQUENCE: 30
gcccttgcta gcgaagcaga ttttaaccca tgtttagtct ctttctttgg atctaatgga    60
atgactctta actgttcatt gtctgcattg tttctcatat tcttcattat tttaaggtct   120
ggaattagtc tataaatggt cgtcgtgatt actcagctca tcctaactt tatatatcat   180
atatatttct actgaagtat tttaaatagt atttagaggt aaaagtctaa gtgaacccaa   240
ctgtaatttc taagctatcc ttatttctgg aagaagaatt ctaccgcatc aaaccagact   300
tttcctagtc cctgagaccc taacttgtga ggtattttag taacatcaca agtcaggctc   360
ttgggaccta ggcggagggg aaccagcagc tttggacctt attgattgtc tgcagttacc   420
accagaacaa agaacatac atagattctg cctaggagaa agaacaatg cttttcttta    480
tcatcagcaa cgttttcacc atgacccatc cccaaaaata ct                     522

<210> SEQ ID NO 31
<211> LENGTH: 71
<212> TYPE: RNA
<213> ORGANISM: Mus musculus

<400> SEQUENCE: 31

| | | | | | |
|---|---|---|---|---|---|
| gccuaguccc | ugagacccua | acuugugagg | uauuuuagua | acaucacaag | ucagguucuu | 60 |
| gggaccuagg | c | | | | | 71 |

<210> SEQ ID NO 32
<211> LENGTH: 6123
<212> TYPE: DNA
<213> ORGANISM: Artificial Sequence
<220> FEATURE:
<223> OTHER INFORMATION: MG-125b1 vector

<400> SEQUENCE: 32

| | | | | | |
|---|---|---|---|---|---|
| tgaaagaccc | cacctgtagg | tttggcaagc | tagcttaagt | aacgccattt | tgcaaggcat | 60 |
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcgg | cgcgccagtc | ctccgataga | ctgcgtcgcc | cgggtacccg | tattcccaat | 420 |
| aaagcctctt | gctgtttgca | tccgaatcgt | ggactcgctg | atccttggga | gggtctcctc | 480 |
| agattgattg | actgcccacc | tcggggggtct | ttcatttgga | ggttccaccg | agatttggag | 540 |
| acccctgcct | agggaccacc | gacccccccg | ccgggaggta | agctggccag | cggtcgtttc | 600 |
| gtgtctgtct | ctgtctttgt | gcgtgtttgt | gccggcatct | aatgtttgcg | cctgcgtctg | 660 |
| tactagttag | ctaactagct | ctgtatctgg | cggacccgtg | gtggaactga | cgagttctga | 720 |
| acacccggcc | gcaaccctgg | gagacgtccc | agggactttg | ggggccgttt | tgtggcccg | 780 |
| acctgaggaa | gggagtcgat | gtggaatccg | accccgtcag | gatatgtggt | tctggtagga | 840 |
| gacgagaacc | taaaacagtt | cccgcctccg | tctgaatttt | tgctttcggt | ttggaaccga | 900 |
| agccgcgcgt | cttgtctgct | gcagcgctgc | agcatcgttc | tgtgttgtct | ctgtctgact | 960 |
| gtgtttctgt | atttgtctga | aaattagggc | cagactgtta | ccactcccct | aagtttgacc | 1020 |
| ttaggtcact | ggaaagatgt | cgagcggatc | gctcacaacc | agtcggtaga | tgtcaagaag | 1080 |
| agacgttggg | ttaccttctg | ctctgcagaa | tggccaacct | ttaacgtcgg | atggccgcga | 1140 |
| gacggcacct | ttaaccgaga | cctcatcacc | caggttaaga | tcaaggtctt | ttcacctggc | 1200 |
| ccgcatggac | acccagacca | ggtcccctac | atcgtgacct | gggaagcctt | ggcttttgac | 1260 |
| ccccctccct | gggtcaagcc | ctttgtacac | cctaagcctc | cgcctcctct | tcctccatcc | 1320 |
| gccccgtctc | tcccccttga | acctcctcgt | tcgaccccgc | ctcgatcctc | cctttatcca | 1380 |
| gccctcactc | cttctctagg | cgccgagatc | tatggtgagc | aagggcgagg | agctgttcac | 1440 |
| cggggtggtg | cccatcctgg | tcgagctgga | cggcgacgtg | aacggccaca | agttcagcgt | 1500 |
| gtccggcgag | ggcgagggcg | atgccaccta | cggcaagctg | accctgaagt | tcatctgcac | 1560 |
| caccggcaag | ctgcccgtgc | cctggcccac | cctcgtgacc | accctgacct | acggcgtgca | 1620 |
| gtgcttcagc | cgctaccccg | accacatgaa | gcagcacgac | ttcttcaagt | ccgccatgcc | 1680 |
| cgaaggctac | gtccaggagc | gcaccatctt | cttcaaggac | gacggcaact | acaagacccg | 1740 |

```
cgccgaggtg aagttcgagg gcgacaccct ggtgaaccgc atcgagctga agggcatcga    1800
cttcaaggag gacggcaaca tcctggggca caagctggag tacaactaca acagccacaa    1860
cgtctatatc atggccgaca gcagaagaa cggcatcaag cgcaacttca agatccgcca    1920
caacatcgag gacggcagcg tgcagctcgc gacactacca gcagaacacc cccatcggcg    1980
acggccccgt gctgctgccc gacaaccact acctgagcac ccagtccgcc ctgagcaaag    2040
accccaacga aagcgcgat cacatggtcc tgctggagtt cgtgaccgcc gccgggatca    2100
ctctcggcat ggacgagctg tacaagtaaa gcggccgcga gttttctctg atgtactcgt    2160
gatcgtatgt gtatgtgcgt gattgtatat gcgcccccag atactgcgta tgtgtgtata    2220
tatgtattag gcttaaacgg aatctcaatt ttgtgaagga aaggagctta gagaagaaat    2280
accataccac ctgtttgttg catcttagtt atgaacctcg aacagaaatt gcctgtcatt    2340
cttgttttgc tttgctttgt ctcaagaaag aaaacattgt tgcgctcctc tcagtccctg    2400
agacccctaac ttgtgatgtt taccgtttaa atccacgggt taggctcttg ggagctgcga    2460
gtcgtgcttt tgcatcctgg aaatttggtg gaattttatt ctttaaagca aaaacaaaag    2520
aaaagaaagt ttgtctgagg tgattgagta tacctctgag gttttcattg ttagatggga    2580
tcaggtgacc agagagtggc agctcctgga tttctgttct cgaggttaac gaatttcgac    2640
ctgcagccaa gcttatcgat aaaataaaag attttatta gtctccagaa aaggggggga    2700
atgaagacc ccacctgtag gtttggcaag ctagcttaag taacgccatt ttgcaaggca    2760
tggaaaatac ataactgaga atagagaagt tcagatcaag gttaggaaca gagagacagc    2820
agaatatggg ccaaacagga tatctgtggt aagcagttcc tgccccggct cagggccaag    2880
aacagatggt ccccagatgc ggtcccgccc tcagcagttt ctagagaacc atcagatgtt    2940
tccagggtgc cccaaggacc tgaaaatgac cctgtgcctt atttgaacta accaatcagt    3000
tcgcttctcg cttctgttcg cgcgcttctg ctcccgagc tcaataaaag agcccacaac    3060
ccctcactcg gcgcgccagt cctccgatag actgcgtcgc ccgggtaccc gtgtatccaa    3120
taaaccctct tgcagttgca tccgacttgt ggtctgctg ttccttggga gggtctcctc    3180
tgagtgattg actaccgtc agcggggtc tttcagtatt cgtaatcatg gtcatagctg    3240
tttcctgtgt gaaattgtta tccgctcaca attccacaca acatacgagc cggaagcata    3300
aagtgtaaag cctggggtgc ctaatgagtg agctaactca cattaattgc gttgcgctca    3360
ctgcccgctt tccagtcggg aaacctgtcg tgccagctgc attaatgaat cggccaacgc    3420
gcggggagag gcggtttgcg tattgggcgc tcttccgctt cctcgctcac tgactcgctg    3480
cgctcggtcg ttcggctgcg gcgagcggta tcagctcact caaaggcggt aatacggtta    3540
tccacagaat caggggataa cgcaggaaag aacatgtgag caaaaggcca gcaaaaggcc    3600
aggaaccgta aaaaggccgc gttgctggcg ttttttccata ggctccgccc cctgacgag    3660
catcacaaaa atcgacgctc aagtcagagg tggcgaaacc cgacaggact ataaagatac    3720
caggcgtttc ccctggaag ctccctcgtg cgctctcctg ttccgaccct gccgcttacc    3780
ggatacctgt ccgcctttct cccttcggga agcgtggcgc tttctcatag ctcacgctgt    3840
aggtatctca gttcggtgta ggtcgttcgc tccaagctgg gctgtgtgca cgaaccccc    3900
gttcagcccg accgctgcgc cttatccggt aactatcgtc ttgagtccaa cccgtaaga    3960
cacgacttat cgccactggc agcagccact ggtaacagga ttagcagagc gaggtatgta    4020
ggcggtgcta cagagttctt gaagtggtgg cctaactacg gctacactag aaggacagta    4080
tttggtatct gcgctctgct gaagccagtt accttcggaa aaagagttgg tagctcttga    4140
```

-continued

```
tccggcaaac aaaccaccgc tggtagcggt ggttttttg tttgcaagca gcagattacg    4200
cgcagaaaaa aaggatctca agaagatcct ttgatctttt ctacggggtc tgacgctcag    4260
tggaacgaaa actcacgtta agggattttg gtcatgagat tatcaaaaag gatcttcacc    4320
tagatccttt taaattaaaa atgaagtttt aaatcaatct aaagtatata tgagtaaact    4380
tggtctgaca gttaccaatg cttaatcagt gaggcaccta tctcagcgat ctgtctattt    4440
cgttcatcca tagttgcctg actccccgtc gtgtagataa ctacgatacg ggagggctta    4500
ccatctggcc ccagtgctgc aatgataccg cgagacccac gctcaccggc tccagattta    4560
tcagcaataa accagccagc cggaagggcc gagcgcagaa gtggtcctgc aactttatcc    4620
gcctccatcc agtctattaa ttgttgccgg gaagctagag taagtagttc gccagttaat    4680
agtttgcgca acgttgttgc cattgctaca ggcatcgtgg tgtcacgctc gtcgtttggt    4740
atggcttcat tcagctccgg ttcccaacga tcaaggcgag ttacatgatc ccccatgttg    4800
tgcaaaaaag cggttagctc cttcggtcct ccgatcgttg tcagaagtaa gttggccgca    4860
gtgttatcac tcatggttat ggcagcactg cataattctc ttactgtcat gccatccgta    4920
agatgctttt ctgtgactgg tgagtactca accaagtcat tctgagaata gtgtatgcgg    4980
cgaccgagtt gctcttgccc ggcgtcaata cgggataata ccgcgccaca tagcagaact    5040
ttaaaagtgc tcatcattgg aaaacgttct cggggcgaa aactctcaag gatcttaccg    5100
ctgttgagat ccagttcgat gtaacccact cgtgcaccca actgatcttc agcatctttt    5160
actttcacca gcgtttctgg gtgagcaaaa acaggaaggc aaaatgccgc aaaaaaggga    5220
ataagggcga cacggaaatg ttgaatactc atactcttcc ttttcaata ttattgaagc    5280
atttatcagg gttattgtct catgagcgga tacatatttg aatgtattta gaaaaataaa    5340
caaatagggg ttccgcgcac atttccccga aaagtgccac ctgacgtcta agaaaccatt    5400
attatcatga cattaaccta taaaaatagg cgtatcacga ggccctttcg tctcgcgcgt    5460
ttcggtgatg acggtgaaaa cctctgacac atgcagctcc cggagacggt cacagcttgt    5520
ctgtaagcgg atgccgggag cagacaagcc cgtcagggcg cgtcagcggg tgttggcggg    5580
tgtcggggct ggcttaacta tgcggcatca gagcagattg tactgagagt gcaccatatg    5640
cggtgtgaaa taccgcacag atgcgtaagg agaaaatacc gcatcaggcg ccattcgcca    5700
ttcaggctgc gcaactgttg ggaagggcga tcggtgcggg cctcttcgct attacgccag    5760
ctggcgaaag ggggatgtgc tgcaaggcga ttaagttggg taacgccagg gttttcccag    5820
tcacgacgtt gtaaaacgac ggccagtgcc acgctctccc ttatgcgact cctgcattag    5880
gaagcagccc agtagtaggt tgaggccgtt gagcaccgcc gccgcaagga atggtgcatg    5940
caaggagatg gcgcccaaca gtcccccggc cacgggcct gccaccatac ccacgccgaa    6000
acaagcgctc atgagcccga agtggcgagc ccgatcttcc ccatcggtga tgtcggcgat    6060
ataggcgcca gcaaccgcac ctgtggcgcc ggtgatgccg gccacgatgc gtccggcgta    6120
gag                                                                  6123
```

REGULATION OF MACROPHAGE ACTIVATION USING MIR-125B

RELATED APPLICATIONS

The present application claims priority under 35 U.S.C. §119(e) to U.S. Provisional Application Nos. 61/499,035, filed Jun. 20, 2011, 61/527,081, filed Aug. 24, 2011, and 61/527,108, filed Aug. 24, 2011. The content of each of these related applications is herein expressly incorporated by reference.

STATEMENT REGARDING FEDERALLY SPONSORED R&D

The invention was made with government support under 1RO1AI079243-01 and 1F32 CA139883-01A1 awarded by National Institutes of Health. The government has certain rights in the invention.

REFERENCE TO SEQUENCE LISTING

The present application is being filed along with a Sequence Listing in electronic format. The Sequence Listing is provided as a file entitled SEQLISTING.TXT, created Jun. 18, 2012, which is 16 Kb in size. The information in the electronic format of the Sequence Listing is incorporated herein by reference in its entirety.

BACKGROUND

1. Field of the Invention

The present disclosure relates generally to activities of microRNA-125b and various uses of miR-125b arising therefrom. For example, miR-125b can be used to modulate innate and adaptive immune responses by regulating activation and/or function of macrophages.

2. Description of the Related Art

MicroRNAs (miRNAs) are a recently discovered class of small RNA molecules that are emerging as potent regulators of multiple aspects of cellular function. mRNAs are evolutionarily conserved and have been found to be involved in post-transcriptional gene repression. See, e.g., Bartel, Cell 116: 281-297 (2004); Ambros, Nature 431: 350-355 (2004); Farh et al., Science 310: 1817-1821 (2005). In animals, miRNAs are processed from larger primary transcripts (pri-miRNA or pri-miR) through an approximate 60-bp hairpin precursor (pre-miRNA or pre-miR) into the mature forms (miRNA) by two RNAse BI enzymes Drosha and Dicer. See, e.g., Gregory et al., Nature 432: 235-40 (2004); Chendrimada et al., Nature 436: 740-744 (2005). The mature miRNA is loaded into the ribonucleoprotein complex (RISC), where it typically guides the downregulation of target mRNA through base pair interactions. Pri-miRNAs are transcribed by RNA polymerase II and predicted to be regulated by transcription factors in an inducible manner. Lee et al., Embo. J., 23: 4051-60 (2004); Fazi et al., Cell 123: 819-31 (2005); O'Donnell, et al., Nature 435: 839-43 (2005). While some miRNAs show ubiquitous expression, others exhibit only limited developmental stage-, tissue- or cell type-specific patterns of expression. See, e.g., Pasquinelli, Curr. Opin. Genet. Dev., 15: 200-205 (2005). In mammals, miRNAs have been associated with diverse biological processes.

Macrophages are key components of the mammalian innate immune system, acting to release cytokines, kill pathogens directly, and present antigens to the adaptive immune system. The macrophage surface contains sensing proteins, like TLRs and IFN-γR that, when engaged, lead to a rapid differentiation event termed activation, in which the cell transforms from relative quiescence to an effector state characterized by far-heightened microbicidal ability. Macrophages also carry co-stimulatory proteins such as CD80 and CD86 for interacting with T cells, thus bridging innate immunity to adaptive immunity. Several microRNAs have been shown to be mediators of the macrophage activation process. O'Connell et al. Nat. Rev. Immunol. 10:111-122 (2010); O'Neill et al., Nat. Rev. Immunol., 11:163-175. miR-155, -146, -147, -9, and -21 are induced by ligands of the TLRs. O'Connell et al., (2010); O'Neill et al., Nat. Rev. Immunol., 11:163-175 (2011). These microRNAs, in turn, inhibit expression of signaling proteins in the inflammatory signaling cascade, thus modulating immunity through feedback regulation. miR-125b, a homolog of the *Caenorhabditis elegans* microRNA lin-4, has been shown to be decreased in macrophages in response to TLR4 signaling. Androulidaki, Immunity, 31: 220-231 (2009); Tili et al., J. Immunol., 179: 5082-5089 (2007); Murphy et al., J. Immunol., 184: 5029-5037 (2010).

SUMMARY

Some embodiments disclosed herein provide a method for activating macrophages in a mammal, wherein the method comprises identifying a mammal in need of macrophage activation; and administering a microRNA-125b (miR-125b) oligonucleotide to macrophages in the mammal, thereby activating the macrophage. In some embodiments, the method further comprises measuring macrophage activation in the mammal.

In some embodiments, the miR-125b oligonucleotide is selected from a mature miR-125b1 oligonucleotide, a mature miR-125b2 oligonucleotide, a pre-miR-125b1 oligonucleotide, a pre-miR-125b2 oligonucleotide, and a miR-125 seed sequence. In some embodiments, the miR-125b oligonucleotide comprises a nucleic acid sequence encoding a miR-125b selected from the group consisting of SEQ ID NOs: 1-7 and 31.

In some embodiments, the administering the miR-125b oligonucleotide to the macrophages comprises contacting the macrophages with an expression construct comprising a nucleic acid encoding the miR-125b oligonucleotide, thereby the miR-125b is expressed in the macrophage.

In some embodiments, the activation of the macrophages comprises T cell activation or inhibiting IRF4 expression in the macrophages. In some embodiments, the activation of macrophages comprises increasing IFN-γ response of the macrophages in the mammal. In some embodiments, the increasing IFN-γ response of the macrophages comprises increasing surface expression of IFN-γ receptor (IFN-γR) on the macrophages.

In some embodiments, the activation of macrophages comprises increasing surface expression of one or more activation markers of the macrophages in the mammal. In some embodiments, the one or more activation markers are selected from MHC II, CD40, CD86, CD80, or any combination thereof.

In some embodiments, the macrophages are selected from alveolar macrophages, histiocytes, kupffer cells microglia, epithelioid cells, osteoclasts, sinusoidal lining cells, giant cells, peritoneal macrophages, tumor associated macrophages (TAM), and a combination thereof. In some embodiments, the macrophages are peritoneal macrophages, TAM, or a combination thereof.

In some embodiments, the mammal suffers from chronic infection or cancer. In some embodiments, the cancer is solid tumor.

Some embodiments disclosed herein provide a method for treating tumor in a mammal in need thereof, comprising administering a microRNA-125b (miR-125b) oligonucleotide to macrophages in the mammal, thereby enhancing activation of macrophages.

In some embodiments, the administering the miR-125b oligonucleotide to the macrophages comprises contacting the macrophages with an expression construct comprising a nucleic acid encoding the miR-125b, thereby the miR-125b oligonucleotide is expressed in the macrophages.

In some embodiments, the miR-125b oligonucleotide comprises a nucleic acid sequence encoding a miR-125b selected from the group consisting of SEQ ID NOs: 1-7 and 31.

Some embodiments disclosed herein provide a method for treating an autoimmune disease in a mammal in need thereof, comprising administering an antisense microRNA-125b (miR-125b) oligonucleotide to macrophages in the mammal, thereby inhibiting activation of macrophages.

In some embodiments, the antisense miR-125b oligonucleotide comprises a nucleic acid sequence encoding an antisense miR-125b selected from the group consisting of SEQ ID NOs: 8-14.

In some embodiments, the autoimmune disease is selected from multiple sclerosis, macrophage activation syndrome, systemic lupus erythematosus, rheumatoid arthritis, and inflammatory bowel disease.

In some embodiments, the administering the antisense miR-125b oligonucleotide to macrophages comprises contacting the macrophages with an expression construct comprising a nucleic acid encoding the antisense miR-125b oligonucleotide, thereby the antisense miR-125b is expressed in the macrophages.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1A shows relative expression of miR-125b in immune tissues and cells as assessed by quantitative PCR. Data represent the mean with SEM of three biological replicates per group. FIG. 1B shows expression of the miR-125b primary transcripts, pri-125b-1 and pri-125b-2, in bone marrow-derived macrophages (BMMs). Data are representative of two independent experiments.

FIG. 3A is a schematic illustration of a retroviral vector MG-125b designed for overexpression of miR-125b-1. FIG. 3B shows relative expression of miR-125b1 in BMMs after transduction with MG or MG-miR-125b1-expressing vector. FIG. 3C shows morphology of control MG or miR-125b1 overexpressing BMMs. Data represent five independent experiments. FIGS. 3D-E show geometric mean fluorescence (GMF) of MHC II, CD40, CD86, and CD80. Representative plots obtained from flow cytometric analyses are also shown for each marker. Data are the mean with SEM of three to five samples per group and represent two independent experiments.

FIG. 5 shows that miR-125b increases macrophage response to IFN-γ.

In FIG. 7A, BMMs expressing the vectors MG or MG-125b were cocultured with OVA-specific OT1 T cells with or without OVA for 72 hours. The percent CD8+ CD25+T cells are shown in the left panel. Concentration of IL-2 (pg/ml) produced by the T cells in the supernatant is shown in the right panel. Data represent the mean with SEM of three biological replicates per group. FIG. 7B shows the percent AnnexinV+EL4-Fluc cells after 94 hours of co-culture with control or miR-125-overexpressing macrophages in the presence of media alone or LPS. A representative flow cytometric plot of the LPS-treated group is shown. Data expressed as mean with SEM of one to three experimental samples per group. In FIGS. 7C-E, EL4-Fluc cells were s.c. coinjected with LPS-activated control or miR-125b-overexpressing macrophages into albino C57BL/6 mice. Tumor surface area in cm2 was monitored from days 9-12 (FIG. 7C). The relative intensity of luminescence (FIG. 7D) and weight (FIG. 7E) of the EL4 tumors was measured on day 12. Data represent the mean plotted with SEM of eight mice per group. The data shown are representative of two independent experiments.

FIG. 8A shows that IRF4 contains a conserved miR-125b target site. FIG. 8B Luciferase reporters carrying the 39 UTR of IRF4, Picalm (negative control), Cut11 (negative control), or 2-mer (positive control) were cotransfected into 293T cells with b-gal reporter and 6 miR-125b. The relative luciferase activity of each reporter in the presence of miR-125b is shown relative to the no miR control. RAW264.7 macrophages were transduced with either a control (MGP) or miR-125b-expressing vector (C) or with control (NC1) or IRF4 shRNA-expressing vector (D). FIGS. 8C-D show L32-normalized IRF4 levels determined by qPCR: RAW264.7 macrophages transduced with a control (MGP) or miR-125b-expressing vector (FIG. 8C), and macrophages transduced with control (NC1) or IRF4 shRNA-expressing vector (FIG. 8D). FIG. 8E shows BMMs expressing MGP, MGP-125b, or shRNA against IRF4 were measured for surface expression of the activation markers MHC II, CD40, CD86, CD80, and IFN-gR. Geometric mean fluorescence (GMF) measured by flow cytometry is shown. All data represent the mean with SEM of three samples per group and are representative of two independent experiments.

DETAILED DESCRIPTION

Figure 1:
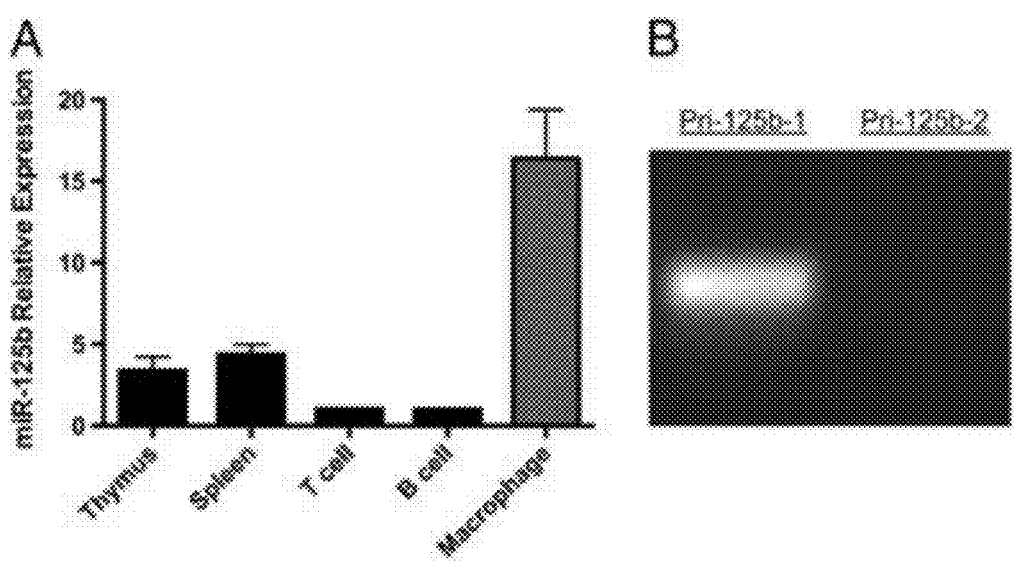
FIG. 1 shows enriched miR-125b expression in macrophages.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are contemplated and make part of this disclosure.

The present disclosure provides miR-125b that is enriched in macrophages as compared with lymphoid cells and whole immune tissues. The miR-125b plays an important role in macrophage activation and various macrophage functions. As disclosed herein, miR-125b can modulate activation and/or functions of macrophages. Through modulation of activation and/or functions of macrophages, miR-125b can modulate, for example, T cell activation, IFN-γ response of macrophages, macrophages' ability to present antigens, surface expression of co-stimulatory molecules of macrophages, and/ or IRF4 expression. The present disclosure also provides methods for treating chronic infections, cancer and autoimmune diseases using miR-125b.

miR-125b can be delivered to macrophages to enhance macrophage activation, which can also enhance T cell activation, enhance IFN-γ response of macrophages, increase macrophages' ability of presenting antigens, increase surface expression of co-stimulatory molecules of macrophages, and/ or inhibit IRF4 expression. In some embodiments, miR-125b is used to treat cancer or chronic infections. In some embodiments, a patient suffering from cancer, such as thymoma, is treated by expressing miR-125b in macrophages, for example, administering a miR-125b oligonucloetide or an expression construct for miR-125b to macrophages. In some embodiments, a patient suffering from a chronic infection, such as tuberculosis, is treated by administering miR-125b to macrophages.

Antisense miR-125b or other miR-125b antagonist can be delivered to macrophages to reduce T cell activation, reduce IFN-γ response of macrophages, inhibit macrophages' ability of presenting antigens, inhibit surface expression of co-stimulatory molecules of macrophages, and/or increase IRF4 expression. In some embodiments, miR-125b antagonists, such as antisense miR-125b, are used to treat autoimmune diseases. In some embodiments, patients suffering from an autoimmune disorder, such as multiple sclerosis (MS), rheumatoid arthritis (RA), inflammatory bowel disease, psoriasis and Systemic Lupus Erythematosus (SLE), are treated by administering a miR-125b antagonist, such as antisense miR-125b to macrophages.

DEFINITIONS

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below.

As used herein, the terms "miR," "mir" and "miRNA" are used to refer to microRNA, a class of small non-coding RNA molecules that are capable of modulating RNA translation (see, e.g., Zeng and Cullen, RNA, 9(1):112-123 (2003); Kidner and Martiennssen, Trends Genet, 19(1):13-6 (2003); Dennis C, Nature, 420(6917):732 (2002); Couzin J, Science 298 (5602):2296-7 (2002), each of which is incorporated by reference herein). The terms "miR," "mir" and "miRNA," unless otherwise indicated, include the mature, pri-, pre-form of a particular microRNA as well as the seed sequence of the microRNA and sequences comprising the seed sequence, and variants thereof. For example, the terms "mRNA-125b" and "miR-125b" are used interchangeably and, unless otherwise indicated, refer to microRNA-125b, including miR-125b, pri-miR-125b, pre-miR-125b, mature miR-125b, miRNA-125b seed sequence, sequences comprising a miRNA-125b seed sequence, and any variants thereof.

As used herein, an "expression vector" refers to a nucleic acid construct, generated recombinantly or synthetically, bearing a series of specified nucleic acid elements that enable transcription of a particular gene in a host cell. Typically, gene expression is controlled using certain regulatory elements, such as constitutive or inducible promoters.

As used herein, "miRNA nucleic acid" refers to a RNA or DNA that encodes a miRNA as defined above, or is complementary to a nucleic acid sequence encoding a miR, or hybridizes to such RNA or DNA and remains stably bound to it under appropriate stringency conditions. For example, miRNA nucleic acids may include genomic DNA, cDNA, mRNA, antisense molecule, pri-miRNA, pre-miRNA, mature miRNA, miRNA seed sequence, as well as nucleic acids based on alternative backbones or including alternative bases. As used herein, miRNA nucleic acids can be derived from natural sources or synthesized.

As used herein, the terms of "microRNA seed sequence," "miRNA seed sequence," "seed region" and "seed portion" are used interchangeably, and refer to nucleotides 2-7 or 2-8 of a mature miRNA sequence. The miRNA seed sequence is typically located at the 5' end of the miRNA.

The term "operably linked" is used herein to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

As used herein, the term "variant" refers to a polynucleotide having a sequence substantially similar to a reference polynucleotide. A variant can comprises deletions or substitutions of one or more nucleotides, and/or additions of one or more nucleotides at the 5' end, 3' end, and/or one or more internal sites in comparison to the reference polynucleotide. Similarities and/or differences in sequences between variants and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variants of a particular polynucleotide disclosed herein, including, but not limited to, a miRNA, will have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans.

As used herein, "mammal" refers to an individual belonging to the class Mammal and includes, but not limited to, humans, domestic and farm animals, zoo animals, sports and pet animals. Non-limiting examples of mammals include humans, mice, rats, sheep, dogs, horses, cats and cows. In some embodiments, the mammal is a human. However, in some embodiments, the mammal is not a human.

As used herein, "treatment" refers to a clinical intervention made in response to a disease, disorder or physiological condition manifested by a patient or to which a patient may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

As used herein, the term "effective amount" refers to an amount sufficient to effect beneficial or desirable biological and/or clinical results.

As used herein, "pharmaceutically acceptable" carriers, excipients, or stabilizers are the ones nontoxic to the cell or mammal being exposed thereto at the dosages and concentrations employed or that have an acceptable level of toxicity as determined by the skilled practitioner. In some embodiments, the physiologically acceptable carrier is an aqueous pH buffered solution. The physiologically acceptable carrier can also comprise one or more of antioxidants, such as ascorbic acid; low molecular weight polypeptides (e.g., less than about 10 residues); proteins, such as serum albumin, gelatin, and immunoglobulins; hydrophilic polymers such as polyvinylpyrrolidone; amino acids; carbohydrates such as glucose, mannose, and dextrins; chelating agents such as EDTA; sugar alcohols such as mannitol or sorbitol; salt-forming counterions such as sodium; and nonionic surfactants such as Tween™, polyethylene glycol (PEG), and Pluronics™.

Abbreviations
  BMM: bone marrow-derived macrophage
  IRF4: IFN regulatory factor 4
  MG: murine stem cell virus GFP
  MGP: murine stem cell virus GFP puromycin
  MHC I: MHC class II
  qPCR: quantitative real-time PCR
  shRNA: short hairpin RNA
  UTR: untranslated region
  Subcutaneous injection: s.c.

MiR-125b Nucleic Acid Molecules

MicroRNA is a class of small non-coding RNA molecules that are capable of modulating RNA translation. Mature miRNAs are typically around 17-25 nucleotides in length, but may be longer or shorter. In nature, miRNAs are generated in cells from miRNA precursors as the result of a series of RNA processing steps. A pri-miRNA transcript having a hairpin structure is first produced. The mature miRNA is located within one arm/strand of this precursor hairpin (the opposite strand of the hairpin, known as the star(*) strand, is generally degraded (see Wang et al., 2008, Dev. Cell, 15, p 261-271)). The pri-miRNA is then processed in the nucleus to form a pre-miRNA which is exported to the cytoplasm. The pre-miRNA undergoes further processing in the cytoplasm to form the mature miRNA. It is in general the mature miRNA that inhibits expression of its target gene at the post-transcriptional level by binding to the mRNA of the target gene by Watson-Crick base pairing. MicroRNAs have been found to have roles in a variety of biological processes including developmental timing, differentiation, apoptosis, cell proliferation, organ development, and metabolism.

As disclosed above, the term "microRNA" used herein refers to the mature, pri-, and pre-form of a microRNA as well as the seed sequence of the microRNA and sequences comprising the seed sequence, and variants thereof. For example, the terms "miRNA-125b" and "miR-125b" are used interchangeably and, unless otherwise indicated, refer to microRNA-125b, including pri-miR-125b, pre-miR-125b, mature miR-125b, miRNA-125b seed sequence, sequences comprising a miRNA-125b seed sequence, and any variants thereof. The mature microRNA may be generated from various precursors, including but not limited to, a primary microRNA transcript (pri-miRNA), a hairpin RNA comprising a miRNA that has been introduced into a cell (including shRNA molecules), or a transcript comprising a microRNA that has been encoded by plasmid DNA that has been introduced into a cell.

Mir-125b is expressed from two loci in both the mouse and human genomes, and these sequences are referred to as miR-125b1 and miR-125b2. In mouse genome, miR-125b1 and miR-125b2 sequences are located on chromosome 9 and 16, respectively. In human genome, miR-125b1 and miR-125b2 sequences are located on chromosome 11 and 21, respectively.

Nucleic acid molecules that encode miR-125b are used in various embodiments. As disclosed herein, a miRNA sequence may comprise from about 6 to about 99 or more nucleotides. In some embodiments, a miRNA sequence comprises about the first 6 to about the first 24 nucleotides of a pre-miRNA-125b1 or a pre-miRNA-125b2, about the first 8 to about the first 22 nucleotides of a pre-miRNA-125b1 or a pre-miRNA-125b2, or about the first 10 to about the first 20 nucleotides of a pre-miRNA-125b1 or a pre-miRNA-125b2. In some embodiments, the miRNA can be an isolated or purified oligonucleotide having at least 6, 7, 8, 10, 11, 12, 13, 14, 15, 16, 17, 18, 19, 20, 21, 22, 23, 24, or 25 nucleotides in length. In some embodiments, the miRNA is a hybridizable portion of a miR-125b coding sequence or its complementary sequence. In some embodiments, the miRNA oligonucleotide has at least 10, 11, 12, 13, 14, 15, 16, 17, 18, 19, 20, 21, 22, 23, 24, or 25 nucleotides. In some embodiments, the miR-125b oligonucleotide has at least 19, 20, 21, 22, 23, 24, or 25 nucleotides. Isolated or purified polynucleotides having at least 6 nucleotides (i.e., a hybridizable portion) of a miR-125b coding sequence or its complement are used in some embodiments. In some embodiments, miR-125b polynucleotides preferably comprise at least 22 (continuous) nucleotides, or a full-length miR-125b coding sequence.

Nucleic acid molecules that encode miR-125b can be used in various embodiments disclosed herein. Sequences for mature miR-125b and pre-miR-125b are provided in SEQ ID NOs: 1, 2, 3, 5, 6, and 31 respectively. Sequences for the seed sequence of miR-125b are provided in SEQ ID NOs 4 and 7, respectively. Human mature miR-125b sequence is set forth in SEQ ID NO: 1, human pre-miR-125b1 sequence is set forth in SEQ ID NO: 2, human pre-miR-125b2 sequence is set forth in SEQ ID NO: 3, human miR-125b seed sequence is set forth in SEQ ID NO: 4, mouse mature miR-125b sequence is set forth in SEQ ID NO: 5, mouse pre-miR-125b1 sequence is set forth in SEQ ID NO: 6, mouse pre-miR-125b2 sequence is set forth in SEQ ID NO: 31, mouse miR-125b seed sequence is set forth in SEQ ID NO: 7. Nucleic acid molecules encoding pri-miR-125b sequences can also be used herein. As disclosed herein, the scope of the present disclosure is not limited to naturally occurring miR-125b sequences; mutants and variants of miR-125b sequences are also covered by the scope of the current disclosure.

It is not intended that the methods disclosed herein be limited by the source of the microRNA. As disclosed herein, the microRNAs can be naturally-occurring or synthetic. In some embodiments, the microRNA can effectively reduce the expression of target polynucleotides through RNA interference. In some embodiments, a synthetic miRNA can have a sequence that is different from a naturally-occurring miRNA and effectively mimic the naturally-occurring miRNA. For example, the synthetic miRNA can have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or greater sequence similarity to the naturally-occurring miRNA. In some embodiments, the microRNA can be a naturally-occurring or synthetic miR-125b1 or miR-125b2. In some embodiments, the microRNA can be a human or mouse miR-125b1 or miR-125b2. For example, miRNA precursors can be purchased from Ambion®.

In some embodiments, a synthetic miRNA can have a sequence that is different from a naturally-occurring miRNA-125b and effectively mimic the naturally-occurring miRNA. For example, the synthetic miRNA can have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or greater sequence similarity to the naturally-occurring miRNA. In other embodiments the synthetic miRNA can have a sequence that is different from the complement of a naturally-occurring miR-125b. For example, the synthetic miRNA can have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or greater sequence similarity to the complement of a naturally-occurring miRNA. For example, the naturally-occurring miRNA can be human mature miR-125b (SEQ ID NO: 1), human pre-miR-125b1 (SEQ ID NO: 2), human pre-miR-125b2 (SEQ ID NO: 3), human miR-125b seed sequence (SEQ ID NO: 4), mouse mature miR-125b (SEQ ID NO: 5), mouse pre-miR-125b1 (SEQ ID NO: 6), mouse pre-miR-125b2 (SEQ ID NO: 31), mouse miR-125b seed sequence (SEQ ID NO: 7).

Nucleotide sequences that encode a variant of a miR-125b, such as a miR-125b with one or more substitutions, additions and/or deletions, and fragments of miR-125b as well as truncated versions of miR-125b maybe also be useful in some of the methods disclosed herein. Preferably, the variant of the miR-125b has at least about 50% of the desired functional activity of the miR-125b. In some embodiments, the variant of the miR-125b has at least about 50%, at least about 60%, at least about 70%, at least about 80%, at least about 90%, at least about 95%, at least about 98% of the desired functional activity of the miR-125b.

Inhibition of miR-125b

The present disclosure provides inhibitors of miR-125b (i.e., anti-miR-125b). Compositions comprising such inhibitors and methods for inhibiting miR-125b using such inhibitors are also disclosed herein. Any miRNA inhibitor may be used alone, or with other miRNA inhibitor(s) known in the art. In some embodiments, the miRNA inhibitor comprises an antisense molecule. Examples of antisense molecule include, but are not limited to, siRNAs, triple-helix-forming agents, ribozymes, RNAi, synthetic peptide nucleic acids (PNAs), antigenes (agRNAs), LNA/DNA copolymers, small molecule chemical compounds, and antisense oligonucleotides.

In some embodiment, the antisense molecule is a triple helix forming agent which is circularized around a double-strand DNA to form a triple helix, thereby inhibiting transcription initiation. In some embodiments, the antisense molecule is a ribozyme which recognizes a specific nucleotide sequence in miR-125b.

In some embodiments, the miRNA inhibitor is a nucleic acid-based inhibitor that is capable of forming a duplex with the target miRNA by Watson-Crick type base pairing. One of the non-limiting examples of the nucleic acid-based miRNA inhibitor is an antisense oligonucleotide. It is not necessary that there be perfect complementarity between the nucleic acid-based miRNA inhibitor and the target miRNA. The miRNA inhibitor may have one or more regions of non-complementarity with the target miRNA flanked by one or more regions of complementarity sufficient to allow duplex formation. In some embodiments, the regions of complementarity can be at least 6, 7, 8, 9, 10, 11, 12, 13, 14, 15, 16, 17, 18, 19, 20, 21, 22, 23, 24, or 25 nucleotides long.

The mechanism by which the miRNA inhibitor functions to inhibit the activity of the target miR-125b is not limited in any way. For example, a nucleic acid-based inhibitor, in some embodiments, may form a duplex with the target miR-125b sequences and prevent proper processing of the mature miR-125b product from its precursor, or may prevent the mature miR-125b from binding to its target gene, or may lead to degradation of pr-, pre-, or mature miRNA, or may act through some other mechanism.

In some embodiments, an inhibitor for miR-125b (for example, an inhibitor for miR-125b1) is used to attenuate, reduce, block, or abolish the activity of the miR-125b. The extent to which the activity of miR-125b is reduced can vary. For example, the miRNA inhibitors disclosed herein can reduce the activity of miR-125b by at least about 10%, at least about 20%, at least about 30%, at least about 40%, at least about 50%, at least about 60%, at least about 70%, at least about 80%, at least about 90%, at least about 95%, at least about 98%, or at least about 99%. In some embodiments, the miRNA inhibitor can completely abolish the activity of miR-125b. Non-limiting examples of miRNA inhibitors include nucleic acids that can block the activity of the target miRNA, such as an antisense miRNA. Such nucleic acids include, for example, antisense miR-125b1 oligonucleotide and antisense miR-125b2 oligonucleotide. Sequence of an exemplary antisense human miR-125b is set forth in SEQ ID NO: 8, sequence of an exemplary antisense mouse miR-125b is set forth in SEQ ID NO: 9, sequence of an exemplary antisense human pre-miR-125b1 is set forth in SEQ ID NO: 10, sequence of an exemplary antisense human pre-miR-125b2 is set forth in SEQ ID NO: 11, sequence of an exemplary antisense mouse pre-miR-125b1 is set forth in SEQ ID NO: 12, sequence of an exemplary antisense human seed miR-125b is set forth in SEQ ID NO: 13, and sequence of an exemplary antisense mouse seed miR-125b is set forth in SEQ ID NO: 14.

In some embodiments, the anti-miRNA can have a total of at least about 5 to about 26 nucleotides. In some embodiments, the sequence of the anti-miRNA can have at least 5, 6, 7, 8, 9, 10, 11, 12, 13, 14, 15, 16, 17, 18, 19, 20, or 21 nucleotides that are substantially complementary to the 5' region of a miR-125b1 or a miR-125b2; at least 5, 6, 7, 8, 9, 10, 11, 12, 13, 14, 15, 16, 17, 18, 19, 20, or 21 nucleotides that are substantially complementary to the 3' region of a miR-125b. In some embodiments, the sequence of the anti-miRNA can comprise at least 4-7 nucleotides that are substantially complementary to a miR-125b seed sequence. In some embodiments, the sequence of the anti-miRNA can comprise at least 5-12 nucleotide that are substantially complementary to the flanking regions of a miR-125b seed sequence. In some embodiments, the anti-miRNA is an antisense miR-125b nucleic acid comprising a total of about 5 to about 100 or more nucleotides, more preferably about 10 to about 60 nucleotides or about 15 to about 30 nucleotides, and has a sequence that is preferably complementary to at least the seed region of miR-125b. It has been shown that antisense miR-NAs can specifically silence target miRNA in tissue. Krutzfeldt, J. et al., Nature, 438:685-9 (2005).

In some embodiments, an anti-miRNA can comprise a total of at least about 5 to about 26 nucleotides. In some embodiments, the sequence of the anti-miRNA can comprise at least 5 nucleotides that are substantially complementary to the 5' region of a miR-125b, at least 5 nucleotides that are substantially complementary to the 3' region of a miR-125b, at least 4-7 nucleotides that are substantially complementary to a miR-125b seed sequence, or at least 5-12 nucleotide that are substantially complementary to the flanking regions of a miR-125b seed sequence.

In some embodiments, an anti-miR-125b is a nucleic acid that comprises the complement of a sequence of a miR-125b referred to in SEQ ID NOs: 1-3, 5, 6, and 31. In some embodiments, the anti-miR-125b is a nucleic acid that comprises the complement of the seed sequence of SEQ ID NO: 4 or 7, or is a nucleic acid that is able to hybridize under stringent conditions to the miRNA-125b seed sequence of SEQ ID NO: 4 or 7. Preferred anti-miR-125b molecules are those that are able to hybridize under stringent conditions to the complement of a cDNA encoding a mature miR-125b, for example SEQ ID NO: 8 or 9. Non-limiting examples of antisense miR-125b1 and miR-125b2 sequences are provide in SEQ ID NOs: 8, 9, 10, 11, 12, 13, and 14.

In some embodiments, a miR-125b antisense oligonucleotide has a sequence that is complementary to a sequence having at least 80%, at least 85%, at least 90%, at least 95%, or at least 98% identity to the mature miR-125b sequence set forth in SEQ ID NO: 1 or 5. In some embodiments, a miR-125b antisense oligonucleotide is able to hybridize, for example under stringent conditions, to a nucleic acid comprising a sequence having at least 80%, at least 85%, at least 90%, at least 95%, or at least 98% identity to the miR-125b sequence set forth in SEQ ID NO: 1 or 5.

In some embodiments, a miR-125b antisense oligonucleotide has a sequence that is complementary to a sequence having at least 80%, at least 85%, at least 90%, at least 95%, or at least 98% identity to the pre-miR-125b sequence set forth in SEQ ID NO: 2, 3, 6, or 31. In some embodiments, a miR-125b antisense oligonucleotide is able to hybridize, for example under stringent conditions, to a nucleic acid comprising a sequence having at least 80%, at least 85%, at least 90%, at least 95%, or at least 98% identity to the pre-miR-125b sequence set forth in SEQ ID NO: 2, 3, 6, or 31.

In some embodiments, a miR-125b antisense oligonucleotide has a sequence that is complementary to a sequence having at least 80%, at least 85%, at least 90%, at least 95%, or at least 98% identity to the seed miR-125b sequence set forth in SEQ ID NO: 4 or 7. In some embodiments, a miR-125b antisense oligonucleotide is able to hybridize, for example under stringent conditions, to a nucleic acid comprising a sequence having at least 80%, at least 85%, at least 90%, at least 95%, or at least 98% identity to the seed miR-125b sequence set forth in SEQ ID NO: 4 or 7.

It is not intended that the methods be limited by the source of the miR-125b or anti-miR-125b. As disclosed herein, the miR-125b or anti-miR-125b can be from a human or non-human mammal, derived from any recombinant source, synthesized in vitro or by chemical synthesis. The nucleic acid can be DNA or RNA, and can in a double-stranded, single-stranded or partially double-stranded form. The miRNA oligonucleotides (e.g., miR-125b and anti-miR-125b oligonucleotides) can be prepared by any conventional means known in the art to prepare nucleic acids. For example, nucleic acids may be chemically synthesized using commercially available reagents and synthesizers by methods that are well-known in the art, including, but not limited to, the phosphotriester method described in Matteucci, et al., (J. Am. Chem. Soc. 103:3185-3191, 1981) and/or an automated synthesis method described in Gait (Oligonucleotide Synthesis: A Practical Approach, 1985, IRL Press, Oxford, England). Larger DNA or RNA segments can also readily be prepared by conventional methods known in the art, such as synthesis of a group of oligonucleotides that define various modular segments, followed by ligation of oligonucleotides to build the complete segment. Unless otherwise indicated, the various embodiments are not limited to naturally occurring miR-125b sequences; mutants and variants of miR-125b sequences may also be used.

The miRNA inhibitor can comprise modified or unmodified nucleotides. In some embodiments, modified nucleotides or backbone modifications can be used to increase stability and/or optimize delivery of the sense or antisense oligonucleotides. Non-limiting modified nucleotides include linked nuclear acid (LNA), 2'-O-Me nucleotides, 2'-O-methoxyethyl, and 2' fluoro. Backbone modifications include, but are not limited to, phosphorothioate and phosphate. In some embodiments, a microRNA or an antisense microRNA oligonucleotide disclosed herein (e.g., miR-125b or anti-miR-125b oligonucleotide) can be modified with cholesterol to enhance delivery to target cells. The cholesterol can be linked, for example, through a hydroxyprolinol linkage on the 3' end of the microRNA.

In some embodiments, the miRNA inhibitor can comprise ribonucleotides, deoxyribonucleotides, 2'-modified nucleotides, phosphorothioate-linked deoxyribonucleotides, peptide nucleic acids (PNAs), locked nucleic acids (LNAs), or other forms of naturally or non-naturally occurring nucleotides. The miRNA inhibitor can comprise nucleobase modifications, include, but not limited to, 2-amino-A, 2-thio (e.g., 2-thio-U), G-clamp modifications, antagomirs, morpholinos, nucleic acid aptamers, or any other type of modified nucleotide or nucleotide derivative that is capable of Watson-Crick type base pairing with a miRNA. As an example, in addition to naturally occurring DNA and/or RNA nucleotide bases, non-naturally occurring modified nucleotide bases that can be used in the miRNA inhibitors disclose herein, include, but are not limited to, 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carb 1 pseudouridine, beta-D-galactosylqueo sine, 2'-Omethylguanosine, inosine, $N^6$-isopente nyladenosine, 1-methyladenosine, 1-methylpseudouridine, 1-methylguanosine, 1-methylaminomethyllinosine, 2,2-dimethylguanosine, 2-methyladenosine, 2-methylguanosine, 3-methylcytidine, 5-methylcytidine, N.sup.6-methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl)carbamoyl)threonine, 2'-O-methyl-5-methyluridine, 2'-O-methyluridine, wybutosine, and 3-(3-amino-3-carboxypropyl) uridine. In some embodiments, the miRNA inhibitor comprises morpholinos or antagomirs.

The miRNA inhibitors disclosed herein can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. A 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

The 5'-terminus of the miRNA inhibitors disclosed herein can also be blocked with an aminoalkyl group, e.g., a 5'-O-alkylamino substituent. Other 5' conjugates can inhibit 5'-3' exonucleolytic cleavage. A 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

The miRNA inhibitors disclosed herein can also be attached to a peptide or a peptidomimetic ligand which may affect pharmacokinetic distribution of the miRNA inhibitor such as by enhancing cellular recognition, absorption and/or cell permeation. The peptide or peptidomimetic moiety can be about 5-50 amino acids long, e.g., about 5, 10, 15, 20, 25, 30, 35, 40, 45, or 50 amino acids long. A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724 (2003)).

In some embodiments, a miR-125b or anti-miR-125b oligonucleotide is modified with cholesterol to enhance delivery to target cells. The cholesterol can be linked, for example, through a hydroxyprolinol linkage on the 3' end of the miRNA.

MicroRNA Expression Constructs

Also disclosed herein are nucleic acid constructs for expressing miR-125b. In some embodiments, expression constructs that comprise an expression vector and a coding sequence for miR-125b or anti-miR-125b inserted therein can be used to deliver the miR-125b or anti-miR-125b to a target cell (e.g., a eukaryotic cells, a mammalian cell, and a mammalian macrophage). In addition to the miR-125b or anti-miR-125b coding sequence, the expression construct may contain one or more additional components, including, but not limited to regulatory elements. Non-limiting examples of the regulatory elements include promoter, enhancer, and other regulatory elements. In some embodiments, the miR-125b or anti-miR-125b coding sequence is optionally associated with a regulatory element that directs the expression of the coding sequence in a target cell. In some embodiments, the expression constructs comprises any of the miR-125b disclosed herein, including but not limited to, the miR-125b provided in SEQ ID NOs: 1-7 and 31. A non-limiting example of the expression constructs is MG-125b1. Sequence of MG-125b1 vector is provided in SEQ ID NO: 32.

It will be appreciated by skilled artisans that the choice of expression vectors and/or regulatory elements to which the miRNA or anti-miRNA encoding sequence is operably linked generally depends on the functional properties desired, e.g., miRNA transcription, and the host cell to be transformed. Examples of expression regulatory elements include, but are not limited to, inducible promoters, constitutive promoters, enhancers, and other regulatory elements. In some embodiments, miR-125b or anti-miR-125b coding sequence is operably linked with an inducible promoter. In some embodiments, the promoter is an elongation factor 1 α (EF1α) promoter, a U6 promoter, or a CMV promoter.

In some embodiments, the expression vector can replicate and direct expression of miR-125b or anti-miR-125b in the target cell, for example macrophages. Various expression vectors that can be used herein include, but are not limited to, expression vectors that can be used for nucleic acid expression in prokaryotic and/or eukaryotic cells. Non-limiting examples of expression vectors for use in prokaryotic cells include pUC8, pUC9, pBR322 and pBR329 available from BioRad Laboratories, (Richmond, Calif.), pPL and pKK223 available from Pharmacia (Piscataway, N.J.). Non-limiting examples of expression vectors for use in eukaryotic cells include pSVL and pKSV-10 available from Pharmacia; pBPV-1/pML2d (International Biotechnologies, Inc.); pcDNA and pTDT1 (ATCC, #31255); viral vectors based on vaccinia virus, poliovirus, adenovirus, adeno-associated virus, herpes simplex virus, a lentivirus; vectors derived from retroviruses such as Rous Sarcoma Virus, Harvey Sarcoma Virus, avian leukosis virus, human immunodeficiency virus, myeloproliferative sarcoma virus, and mammary tumor virus); and the like. Additional examples of suitable eukaryotic vectors include bovine papilloma virus-based vectors, Epstein-Barr virus-based vectors, SV40, 2-micron circle, pcDNA3.1, pcDNA3.1/GS, pYES2/GS, pMT, p IND, pIND (Sp1), pVgRXR (Invitrogen), and the like, or their derivatives.

In some embodiments, the expression construct integrates into the genome of the host cell (e.g., a macrophage). In some embodiments, the expression construct is maintained extra-chromosomally in the host cell comprising the expression construct. A host cell (e.g., a macrophage) comprising a subject recombinant vector is referred to as a "genetically modified" host cell herein.

In some embodiments, the expression vectors disclosed herein can include one or more coding regions that encode a polypeptide (a "marker") that allows for detection and/or selection of the genetically modified host cell comprising the expression vectors. The marker can be, for example, a drug resistance protein such as neomycin phosphotransferase, aminoglycoside phosphotranferase (APH); a toxin; or a labeled polypeptide, such as a fluoresccnctly labeled polypeptide. Various selection systems that are well known in the art can be used herein. The selectable marker can optionally be present on a separate plasmid and introduced by co-transfection.

Expression control elements that can be used for regulating the expression of an operably linked coding sequence are known in the art and include, but are not limited to, inducible promoters, constitutive promoters, enhancers, and other regulatory elements. In some embodiments an inducible promoter is used that is readily controlled, such as being responsive to a nutrient in the target cell's medium. In some embodiments, the promoter is the U6 promoter or CMV promoter. In some embodiments, the promoter is a tissue-specific promoter. In some embodiments, the promoter is a promoter specific to a target cell type. In some embodiments, the promoter is a promoter specific to macrophages.

Skilled artisans will appreciate that any methods, expression vectors, expression control elements and target cells suitable for adaptation to the expression of a miRNA or anti-miRNA in target cells can be used herein and can be readily adapted to the specific circumstances.

Delivery of MicroRNA Oligonucleotides and Expression Constructs to a Target Cell or a Tissue In some embodiments, a miR-125b or anti-miR-125b oligonucleotide is delivered to a target cell, tissue or organ. In some embodiments, an expression construct encoding the miR-125b or the anti-miR-125b is delivered to a target cell, tissue or organ where the miR-125b or anti-miR-125b is expressed. In some embodiments, delivery is systemic and the oligonucleotide or expression vector is taken up into target cells, tissues or organs where it has a desired activity. In some such embodiments, the oligonucleotide or expression vector may be taken up by non-target cells or tissues, but preferably does not have a significant negative effect on such cells or tissues, or on the organism as a whole.

Methods for delivery of oligonucleotides and expression constructs to target cells are known in the art and non-limiting exemplary methods are described briefly below. Target cells can be, for example, any stem or progenitor cells, such as macrophages. Target cells may be present in a host, such as in a mammal; or may be in culture outside of a host. In some embodiments, the miR-125b or anti-miR-125b oligonucleotide or expression construct is delivered to the target cell in vivo. In some embodiments, the miR-125b or anti-miR-125b oligonucleotide or expression construct is delivered to the target cell ex vivo. In some embodiments, the miR-125b or anti-miR-125b oligonucleotide or expression construct is delivered to the target cell in vitro.

In some embodiments, the target cell is a macrophage. The type or location of the macrophage is not limited. Examples of the macrophage include, but are not limited to, dust cells/alveolar macrophages, histiocytes, kupffer cells microglia, epithelioid cells, osteoclasts, sinusoidal lining cells, giant cells, tumor associated macrophages (TAM), and peritoneal macrophages. The macrophage can be located at, for example, lungs (e.g., pulmonary alveolus of lungs), connective tissues, liver, neural tissue, granulomas, bone, spleen, peritoneal cavity. Target cells may be present in a host, such as in a mammal, or may be in culture outside of a host. Delivery of miR-125b or anti-miR-125b to target cells in vivo, ex vivo and in vitro is contemplated, depending on the particular circumstances.

In some embodiments, the miR-125b or anti-miR-125b oligonucleotides or expression constructs are delivered to a target organ or tissue. Non-limiting examples of target organs and tissues include organs and tissues where hematopoietic and/or immune cells or precursors of such cells are known to be located and may include, for example and without limitation, the peritoneal cavity, spleen, lymph nodes, including mesenteric lymph nodes and peripheral lymph nodes, thymus, and bone marrow. In some embodiments the target tissue is a tissue undergoing autoimmune inflammation. Tissue that may be undergoing inflammation is not limited in any way and may be, for example, tissues of the central nervous system, skin, instestines, joints, kidneys and the like. In some embodiments, miR-125b or anti-miR-125b oligonucleotides or expression constructs are delivered to tissues undergoing autoimmune inflammation. In some embodiments miR-125b or anti-miR-125b are delivered systemically, such as by intravenous injection. Additional routes of administration may include, for example, oral, topical, intrathecal, intraperitoneal, intranasal, intraocular, and intramuscular. Other routes of administration are well known in the art and will be apparent to the skilled artisan. In some embodiments, miR-125b or anti-miR-125b oligonucleotides or expression constructs can be delivered ex vivo to macrophages harvested from a patient. In some embodiments, the macrophages are harvested from one site of the patient and the macrophages containing the miR-125b or anti-miR-125b oligonucleotides or expression constructs are reintroduced to the same site of the patient. In some embodiments, the macrophages are harvested from a first site of the patient and the macrophages containing the miR-125b or anti-miR-125b oligonucleotides or expression constructs are reintroduced to a second site of the patient, wherein the first site and the second site are different.

Delivery of oligonucleotides and/or expression constructs to a target cell can be achieved in a variety of ways. In some embodiments, a transfection agent is used. As used herein, the terms "delivery vehicle," refers to a compound or compounds that enhance the entry of oligonucleotides and polynucleotides into cells. Examples of delivery vehicle of miRNA, anti-miRNA and expression constructs, include, but are not limited to, protein and polymer complexes (polyplexes), combinations of polymers and lipids (lipopolyplexes), multilayered and recharged particles, lipids and liposomes (lipoplexes, for example, cationic liposomes and lipids), polyamines, calcium phosphate precipitates, polycations, histone proteins, polyethylenimine, polylysine, and polyampholyte complexes. One example of transfection reagent suitable for delivery of miRNA is siPORT™ NeoFX™ Transfection Agent (Ambion, Inc.), which can be used to transfect a variety of cell types with miRNA. miRNAs can be readily electroporated into primary cells without inducing significant cell death. miRNAs can be transfected at various concentrations. The transfection efficiency of synthetic miRNAs has been shown to be very good, and around 100% for certain cell types (Ambion, Inc. miRNA Research Guide, page 12).

In some embodiments, the delivery vehicle comprises a transfection agent. Transfection agents may be used to condense nucleic acids. Transfection agents may also be used to associate functional groups with a polynucleotide. Non-limiting examples of functional groups include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers). For delivery in vivo, complexes made with sub-neutralizing amounts of cationic transfection agent can be used.

In some embodiments, polycations are mixed with the miRNA or the anti-miRNA oligonucleotide disclosed herein for delivery to a target cell. Polycations are a very convenient linker for attaching specific receptors to DNA and as result, DNA/polycation complexes can be targeted to specific cell types. Here, targeting is preferably to cells involved in innate immunity. An endocytic step in the intracellular uptake of DNA/polycation complexes is suggested by results in which functional DNA delivery is increased by incorporating endosome disruptive capability into the polycation transfection vehicle. Polycations also cause DNA condensation. The volume which one DNA molecule occupies in complex with polycations is drastically lower than the volume of a free DNA molecule. The size of DNA/polymer complex may be important for gene delivery in vivo. In some embodiments, the miRNA or the anti-miRNA oligonucleotide and one or more transfection reagents are delivered systematically such as by injection. In some embodiments, the miRNA or the anti-miRNA oligonucleotide can be injected into particular areas comprising target cells, such as particular organs, for example the bone marrow.

In some embodiments, the miRNA, anti-miRNA or expression construct can be delivered systemically. In some embodiments, the miRNA, anti-miRNA or expression construct can be delivered in combination with one or more pharmaceutically acceptable carriers. In some embodiments, the miRNA, anti-miRNA or expression construct can be injected intravenously.

Polymer reagents for delivery of the miRNA, anti-miRNA and expression vectors may incorporate compounds that increase their utility. These groups can be incorporated into monomers prior to polymer formation or attached to polymers after their formation. A vector transfer enhancing moiety is typically a molecule that modifies a nucleic acid complex and can direct it to a cell location (such as tissue cells) or location in a cell (such as the nucleus) either in culture or in a whole organism. By modifying the cellular or tissue location of the complex, the desired localization and activity of the miRNA, anti-miRNA or expression vector can be enhanced. The transfer enhancing moiety can be, for example, a protein, a peptide, a lipid, a steroid, a sugar, a carbohydrate, a nucleic acid, a cell receptor ligand, or a synthetic compound. The transfer enhancing moieties can, in some embodiments, enhance cellular binding to receptors, cytoplasmic transport to the nucleus and nuclear entry or release from endosomes or other intracellular vesicles.

Nuclear localizing signals (NLSs) can also be used to enhance the targeting of the miRNA, anti-miRNA or expression vector into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors such as the NLS receptor (karyopherin alpha) which then interacts with karyopherin beta. The nuclear transport proteins themselves can also, in some embodiments, function as NLS since they are targeted to the nuclear pore and nucleus.

Compounds that can cause or enhance release of nucleic acids from intracellular compartments such as endosomes (early and late), lysosomes, phagosomes, vesicle, endoplasmic reticulum, Golgi apparatus, trans Golgi network (TGN), and sarcoplasmic reticulum can be used to aid delivery of miRNA-125b or anti-miR-125b or expression vectors. The release includes movement out of an intracellular compartment into cytoplasm or into an organelle such as the nucleus. Examples of such compounds include, but are not limited to, chemical compounds such as chloroquine, bafilomycin, Brefeldin Al; ER-retaining signal (KDEL sequence); viral components such as influenza virus hemagglutinin subunit HA-2 peptides; and other types of amphipathic peptides.

Cellular receptor moieties are any signal that enhances association of the miRNA, anti-miRNA or expression vector with a cell. Enhanced cellular association can be accomplished by either increasing the binding of miRNAs, anti-mRNAs, or expression constructs encoding miRNA or anti-miRNA to the cell surface and/or their association with an intracellular compartment. For example, enhanced cellular association can be achieved by ligands that enhance endocytosis. Cellular receptor moieties include agents that target to asialoglycoprotein receptors by using asialoglycoproteins or galactose residues. Viral proteins, proteins such as insulin, EGF, or transferring; peptides that include the RGD sequence; chemical groups that react with sulfhydryl or disulfide groups on cells; folate and other vitamins can also be used for targeting. Other non-limiting targeting groups include molecules that interact with membranes such as lipids fatty acids, cholesterol, dansyl compounds, and amphotericin derivatives.

Skilled artisans will be able to select and use an appropriate system for delivering miRNA-125b or anti-miRNA-125b or an expression vector to target cells in vitro, ex vivo, or in vivo without undue experimentation.

Modulation of Macrophage Activation

As disclosed herein, miRNA-125b can be used to modulate macrophages activation. In some embodiments, macrophage activation can be modulated by administering miR-125b or an antisense miR-125b oligonucloetide to macrophages. As discussed below, one or more activities of macrophages can be increased or decreased by administering miR-125b or an antisense miR-125b oligonucloetide to the macrophages. The macrophages can be in a mammal. Various miR-125b disclosed herein can be used to modulate macrophages activation. For example, the miR-125b can be one miR-125b or anti-miR-125b provided in SEQ ID NO: 1-14 or a mixture thereof.

Variants of the miR-125b or antisense miR-125b disclosed and fragments thereof can also be used in the methods disclosed herein. The effects of miR-125b or anti-miR-125b on modulation of macrophage activation or function can be measured by detecting, for example, T cell activation; IFN-γ response of the macrophages (e.g., IFN-γ secretion, IFN-γR production); expression of macrophage activation markers, including MHC II, CD40, CD86, and CD80; antigen-presenting ability of the macrophages; and IRF4 expression of the macrophages. In some embodiments, increased activation of macrophages is shown by increased T cell activation, increased IFN-γ response of the macrophages, increased expression of macrophage activation markers, decreased IRF4 expression, and/or increased antigen-presenting ability of the macrophages. In some embodiments, decreased activation of macrophages is shown by decreased T cell activation, decreased IFN-γ response of the macrophages, decreased expression of macrophage activation markers (e.g., surface examples of co-stimulatory markers), increased IRF4 expression, and/or decreased antigen-presenting ability of the macrophages In some embodiments, miR-125b or antisense miR-125b oligonucleotide can be administered by contacting macrophages with an expression contract comprising a nucleic acid encoding the miR-125b or antisense miR-125b, such that the miR-125b or antisense miR-125b is expressed in the macrophages.

In some embodiments, macrophages activation can be regulated by delivering a miR-125b to the macrophages. In some embodiments, the miR-125b is miR-125b1, miR-125b2, or a mixture thereof. In some embodiments, macrophages activation can be regulated by delivering an antisense miR-125b oligonucleotide to the macrophages, wherein the antisense miR-125b oligonucleotide is antisense miR-125b1 or antisense miR-125b2. Macrophages activation can be either up-regulated or down-regulated.

In some embodiments, macrophages activation is upregulated by administering an oligonucleotide or expression construct for miR-125b to macrophages, macrophage-containing tissues or macrophage-containing organs. Non-limiting examples of macrophage activity include T cell activation, IFN-γ response, antigen-presenting activity, surface expression of co-stimulatory molecules (e.g., CD80), and inhibiting IRF4 expression. Increased T cell activation, increased IFN-γ response of the macrophage, increased macrophages' ability of presenting antigens, and increased surface expression of co-stimulatory molecules can be measured by methods known in the art after administering an oligonucleotide or expression construct for miR-125b, to macrophages, macrophages-containing tissues or macrophages-containing organs. Decreased expression of IRF4 can also be measured by methods known in the art after administering an oligonucleotide or expression construct for miR-125b, to macrophages, macrophages-containing tissues or macrophages-containing organs. In some embodiments, macrophage activation can be increased by administering miR-125b1, miR-125b2, or a mixture thereof to macrophages in peritoneum or elsewhere.

In some embodiments, activity of macrophages is down-regulated by administering an oligonucleotide or expression construct for an antisense miR-125b, to macrophages, macrophages-containing tissues or macrophages-containing organs. Decreased surface expression of co-stimulatory molecules, including CD80, can be detected, for example, by FACS analysis after administering the antisense miR-125b to macrophages, macrophages-containing tissues or macrophages-containing organs. Decreased T cell activation, decreased IFN-γ response of the macrophage, decreased macrophages' ability of presenting antigens, and increased IRF expression can be measured by methods known in the art after administering an oligonucleotide or expression construct for anti-miR-125b, to macrophages, macrophages-containing tissues or macrophages-containing organs.

Skill artisans will appreciate that, in some circumstances, the up-regulation or down-regulation of macrophage activation caused by the administration of miR-125b or anti-miR-125b oligonucleotide to macrophages can be dose-dependent. The effective amount of the miRNA oligonucleotide for up-regulating or downregulating macrophage activation can be determined by skilled artisan using knowledge and techniques known in the art without undue experimentation.

Any of the sequences of miR-125b or antisense miR-125b disclosed herein and variants thereof can be used to regulate proliferation, activity and/or function of macrophages. In some embodiments, the miR-125b oligonucleotide comprises all or a portion of mature miR-125b, pre-miR-125b1, pre-miR-125b2, pri-miR-125b1, pri-miR-125b2, or a miR-125b seed sequence. Mixtures of various miR-125b nucleic acids can also be used. In some embodiments, the miR-125b has at least about 80%, about 85%, about 90%, about 95%, or about 98% sequence identity to a sequence selected from the group consisting of SEQ ID NOs: 1, 2, 3, 4, 5, 6, 7, and 31. In some embodiments, the miR-125b comprises all or a portion of a sequence selected from the group consisting of SEQ ID NOs: 1, 2, 3, 4, 5, 6, 7, and 31. In some embodiments, the miR-125b expression construct comprises a sequence encoding a miR-125b selected from the group consisting of SEQ ID NOs: 1, 2, 3, 4, 5, 6, and 7. In some embodiments, the antisense miR-125b is complementary to all or a portion of SEQ ID NOs: 1, 2, 3, 4, 5, 6, 7, and 31. In some embodiments, the antisense miR-125b hybridizes under stringent conditions to one or more of SEQ ID NOs: 1, 2, 3, 4, 5, 6, 7, and 31. In some embodiments, the antisense miR-125b has at least about 80%, about 85%, about 90%, about 95%, or about 98% sequence identity to a sequence selected from the group consisting of SEQ ID NOs: 8, 9, 10, 11, 12, 13, and 14.

In some embodiments, mixtures of various miR-125b nucleic acids can be used.

As disclosed herein, T cell activation in a subject can be regulated by administering an oligonucleotide or expression construct for a miR-125b or an antisense miR-125b to macrophages in peritoneum or elsewhere. The miR-125b can be miR-125b1, miR-125b2, or a mixture thereof. The T cell activation can be either increased or down-regulated. In some embodiments, the T cell activation is increased by administering a miR-125b oligonucleotide to the macrophages. In some embodiments, the T cell activation is down-regulated by administering the oligonucleotide or expression construct for the antisense miR-125b to the macrophages. The upregulation or down-regulation of the T cell activation can, in some embodiments, be determined by measuring the number of $CD8^+CD25^+$ T cells or IL-2 secretion by the T cells in response to antigen. Skill artisans will appreciate that, in some circumstances, the upregulation or downregulation in the T cell activation caused by the administration of miR-125b or an anti-miR-125b oligonucleotide to macrophages can be dose-dependent. The effective amount of miRNA or antisense oligonucleotide for enhancing or down-regulating the T cell activation can be determined by skilled artisans using knowledge and techniques known in the art without undue experimentation.

As disclosed herein, IFN-γ response of macrophages in a subject is regulated by administering a miR-125b or an anti-miR-125b oligonucleotide to macrophages in peritoneum or elsewhere. The miR-125b can be miR-125b1, miR-125b2, or a mixture thereof. The IFN-γ response can be either increased or decreased. In some embodiments, the IFN-γ response is increased by administering a miR-125b oligonucleotide to the macrophages. In some embodiments, the IFN-γ response is down-regulated by administering an anti-miR-125b oligonucleotide to the macrophages. The increase or decrease of the IFN-γ response can, in some embodiments, be determined by measuring the surface expression of IFN-γR, or the surface expression of macrophage activation marker (e.g., MHC II, CD40, CD86, and CD80). Skilled artisans will appreciate that, in some circumstances, the upregulation or down-regulation in the IFN-γ secretion caused by the administration of miR-125b or an anti-miR-125b oligonucleotide to macrophages can be dose-dependent. The effective amount of miRNA or antisense oligonucleotide for enhancing or down-regulating the IFN-γ response of macrophages can be determined by skilled artisans using knowledge and techniques known in the art without undue experimentation.

As disclosed herein, macrophages' antigen-presenting ability in a subject is regulated by administering a miR-125b or an anti-miR-125b oligonucleotide to macrophages in peritoneum or elsewhere. The miR-125b can be miR-125b1, miR-125b2, or a mixture thereof. The macrophages' antigen-presenting ability can be either increased or decreased. In some embodiments, the macrophages' antigen-presenting ability is increased by administering a miR-125b oligonucleotide to the macrophages. In some embodiments, the macrophages' antigen-presenting ability is down-regulated by administering an anti-miR-125b oligonucleotide to the macrophages. The increase or decrease of the macrophages' antigen-presenting ability, in some embodiments, be determined by measuring the number of $CD25^+$ T cells or IL-2 secretion by the T cells in response to antigen. Skill artisans will appreciate that, in some circumstances, the upregulation or downregulation in the macrophages' antigen-presenting ability caused by the administration of miR-125b or an anti-miR-125b oligonucleotide to macrophages can be dose-dependent. The effective amount of miRNA or antisense oligonucleotide for enhancing or down-regulating the macrophages' antigen-presenting ability can be determined by skilled artisans using knowledge and techniques known in the art without undue experimentation.

As disclosed herein, surface expression of co-stimulatory molecules on macrophages in a subject can be regulated by administering a miR-125b or an anti-miR-125b oligonucleotide to macrophages in peritoneum or elsewhere. The miR-125b can be miR-125b1, miR-125b2, or a mixture thereof. The surface expression of co-stimulatory molecules on the macrophages can be either increased or decreased. In some embodiments, the surface expression of co-stimulatory molecules on the macrophages is increased by administering a miR-125b oligonucleotide to the macrophages. In some embodiments, the surface expression of co-stimulatory molecules on the macrophages is down-regulated by administering an anti-miR-125b oligonucleotide to the macrophages. The increase or decrease of the surface expression of co-stimulatory molecules on the macrophages, in some embodiments, be determined by FACS analysis to detect the surface expression of markers such as MHC II, CD40, CD86, and CD80 on the macrophages. Skilled artisans will appreciate that, in some circumstances, the upregulation or downregulation in the surface expression of co-stimulatory molecules on macrophages caused by the administration of an oligonucleotide or expression vector for an miR-125b or an anti-miR-125b to macrophages can be dose-dependent. The effective amount of miRNA or antisense oligonucleotide for enhancing or down-regulating the surface expression of co-stimulatory molecules on macrophages can be determined by skilled artisans using knowledge and techniques known in the art without undue experimentation.

As disclosed herein, IRF4 expression in macrophages in a subject can be regulated by administering a miR-125b or an anti-miR-125b oligonucleotide to macrophages in peritoneum or elsewhere. The miR-125b can be miR-125b1, miR-125b2, or a mixture thereof. The IRF4 expression in macrophages can be either increased or decreased. In some embodiments, the IRF4 expression in macrophages is reduced by administering a miR-125b oligonucleotide to the macrophages. In some embodiments, the IRF4 expression in macrophages is increased by administering an anti-miR-125b oligonucleotide to the macrophages. Skill artisans will appreciate that, in some circumstances, the increase or decrease in the IRF4 expression in macrophages caused by the administration of miR-125b or an anti-miR-125b oligonucleotide to macrophages can be dose-dependent. The effective amount of miRNA or antisense oligonucleotide for increasing or decreasing the IRF4 expression in macrophages can be determined by skilled artisans using knowledge and techniques known in the art without undue experimentation.

In some embodiments, miR-125b can be used to treat subjects with low macrophage activity and/or function, for example, low phagocytic activity, low antigen-presenting ability, or low ability to degrade bacterial antigen. As disclosed above, low macrophage activity and/or function in a subject can be increased by administering miR-125b oligonucleotide to macrophages in peritoneum or elsewhere, thereby increase the activity or function of macrophages in the subject. Examples of diseases or disorders of low macrophage activity and/or function include, but are not limited to chronic infections, such as tuberculosis, paratuberculosis, Whipple's disease, Leishmaniasis; heart diseases, such as atherosclerosis; HIV infection; cancer, such as solid tumor including, but not limited to, sarcomas, carcinomas, lymphomas, and thymoma.

In some embodiments, activation and/or one or more functions of macrophages in a subject can be reduced or inhibited by administering an anti-miR-125b oligonucleotide to macrophages in peritoneum or elsewhere. In some embodiments, the miRNA is miR-125b1, miR-125b2, or a mixture thereof. In some embodiments, miR-125b can be used to treat subjects with abnormally high macrophage activity and/or function, for example, autoimmune diseases. Non-limiting examples of autoimmune disease include multiple sclerosis, macrophage activation syndrome, encephalomyelitis (e.g., acute disseminated encephalomyelitis, encephalomyelitis disseminate, equine encephalomyelitis, myalgic encephalomyelitis, and experimental autoimmune encephalomyelitis), rheumatoid arthritis, and inflammatory bowel disease.

The miRNA-125b or antisense miRNA-125b can be delivered as described herein or as known in the art. In some embodiments, delivery can be achieved by modification of an oligonucleotide encoding the miRNA-125b or antisense miRNA-125b. For example, a miR-125b, such as a mature miR-125b1 or miR-125b2, can be attached with cholesterol to facilitate penetration of the miR-125b into the cell membrane. Delivery can be optimized by using modified nucleotides or utilizing backbone modifications. Delivery can be achieved by injection into particular areas such as hematopoietic tissue or the bone marrow.

As disclosed herein, miR-125b over-expressing macrophages are more effective in killing tumor cells, for example thymoma tumor cells, as compared to wildtype macrophages. Some embodiments disclosed herein provide methods for treating cancer, for example solid tumor, in a mammal, where the method comprises administering miR-125b (e.g., a miR-125b oligonucleotide) to macrophages in the mammal, thereby enhancing apoptosis of cancer cells in the mammal. In some embodiments, the miR-125b is miR-125b1 or miR-125b2 oligonucleotide. In some embodiments, the cancer is solid tumor. Non-limiting examples of solid tumor includes, but are not limited to, sarcomas, carcinomas, lymphomas, and thymoma.

EXAMPLES

Additional embodiments are disclosed in further detail in the following examples, which are not in any way intended to limit the scope of the claims.

Experimental Materials and Methods

The following experimental material and methods were used for Examples 1-5 described below.

Cell Culture 293T cells, RAW264.7 cells, and BMMs were cultured at 37° C. with 5% $CO_2$ in DMEM supplemented with 10% FBS, 100 U/ml penicillin, and 100 U/ml streptomycin. For IFN-γ treatment, cells were treated overnight with 200 U/ml recombinant mouse IFN-γ (eBioscience).

Isolation of Immune Cells and Tissues

T cells and B cells were purified from the spleens of C57BL/6 mice using magnetic beads (Miltenyi Biotec). Peritoneal macrophages were isolated 4 days after injecting mice with 3% thyoglycollate.

DNA Constructs

The murine stem cell virus GFP (MG), murine stem cell virus puromycin GFP (MGP), MG-125b-1, and MGP-125b-1 vector systems were described in O'Connell et al., Proc. Natl. Acad. Sci. USA 107: 14235-14240 (2010); O'Connell et al., J. Exp. Med. 205: 585-594 (2008); O'Connell et al., Proc. Natl. Acad. Sci. USA, 106: 7113-7118 (2009). Human miR-125b-1 sequence was cloned into the pcDNA3 vector downstream of the CMV promoter. IRF4 short hairpin RNA (shRNA) sequence was predicted and cloned into MGP as described in O'Connell et al. (2009) and Rao et al., Immunity 33:48-59 (2010). NC1 is a negative control shRNA sequence predicted not to target any protein coding genes in the mouse genome (Invitrogen). For reporter assays, pMIR-REPORT vector (Ambion) containing Picalm and Cut11 39 untranslated regions (UTRs) described in O'Connell et al. (2008) was used. A 3-kb region of the human IRF4 39 UTR, which includes the miR-125b putative binding site, was cloned into pMIR-REPORT downstream of luciferase. A positive control 2-mer containing two tandem sites complementary to miR-125b was also cloned. Primer sequences are listed in Table 1.

TABLE 1

Oligonucleotide and PCR Primer Sequences

| Primer | Sequence |
| --- | --- |
| IRF4 shRNA oligo | GAAGGCTGTATGCTGAAACAATGCCCAAGCCTTGAA GTTTTGGCCACTGACTGACTTCAAGGCGGGCATTGTT TCAGGACACAAGGCCTG (SEQ ID NO: 20) |
| IRF4 3' UTR NOTI FW | TTCGCGGCCGCGAGTTTTCTCTGATGTACTCGTGATC GTATGT (SEQ ID NO: 21) |
| IRF4 3' UTR XHOI REV | TTCCTCGAGAACAGAAATCCAGGAGCTGCCACTC (SEQ ID NO: 22) |
| 2MER SPEI FW | CTAGTTCACAAGTTAGGGTCTCAGGGATCACAAGTT AGGGTCTCAGGGAA (SEQ ID NO: 23) |
| 2MER HINDIII REV | AGCTTTCCCTGAGACCCTAACTTGTGATCCCTGAGA CCCTAACTTGTGAA (SEQ ID NO: 24) |
| IRF4 QPCR FW | TCCGACAGTGGTTGATCGAC (SEQ ID NO: 25) |
| IRF4 QPCR REV | CCTCACGATTGTAGTCCTGCTT (SEQ ID NO: 26) |
| L32 QPCR FW | AAGCGAAACTGGCGGAAAC (SEQ ID NO: 27) |
| L32 QPCR REV | TAACCGATGTTGGGCATCAG (SEQ ID NO: 28) |

Retrovirally Transduced Bone Marrow-Derived Macrophages

To generate retrovirus for infecting bone marrow, 293T cells were transfected with pCL-Eco and MG, MGP, MG-125b-1, or MGP-125b-1 vectors. After 36 hours, 10 mg/ml polybrene (Millipore) was added to retrovirus-containing culture supernatant, which was used to spin-infect bone marrow from C57BL/6 mice. Cells were counted, and 1 million were plated per well in a six-well plate with 10 ng/ml M-CSF (eBioscience) and differentiated for 6 days to yield retrovirally transduced bone marrow-derived macrophages (BMMs).

Stable Cell Lines

RAW264.7 cells were stably transduced with vesicular stomatitis virus-G-pseudotyped MGP or MGP-125b-1 retrovirus, and puromycin selection was subsequently performed as described in O'Connell et al., Proc. Natl. Acad. Sci. USA, 106:7113-7118 (2009).

Electroporation of Anti-miR5

RAW264.7 cells were coelectroporated with anti-miR-125b or a mismatched control (Regulus Therapeutics) and pmaxGFP vector (Lonza) using an Amaxa Nucleofector (Amaxa). Thirty-six hours postelectroporation, GFP-positive cells were analyzed by FACS. Anti-miR-125b or mismatched control compound were chimeric 29-fluoro/29-O-methoxy-ethyl-modified oligonucleotides with a completely modified phosphorothioate backbone (Regulus Therapeutics).

T Cell Macrophage Coculture

A total of 50,000 BMMs stably expressing either MG or MG-125b-1 were cocultured with 150,000 T cells harvested from OTI OVA TCR-transgenic BALB/c mouse in a 48-well flat-bottom plate in the absence or presence of OVA protein. Flow cytometry and ELISAs to assess T cell activation were performed 72 hours later. ELISAs were performed with an IL-2 detection kit from eBioscience and carried out according to the manufacturer's instructions.

EL4 Tumor Cell Experiments

A total of 500,000 BMMs stably expressing either MG or MG-125b-1 were generated per well in six-well plates. One million EL4-Fluc cells were added to each well supplemented with 20 ng/ml LPS. EL4-Fluc apoptosis was measured 94 hours later by staining cells in suspension with Annexin VAb (BD Pharmingen). For the in vivo experiments, 2 million EL4-Fluc cells ere co-injected with 400,000 BMMs s.c. into albino C57BL/6 mice. Mice ere closely monitored over the next 12 days. Tumor luminescence was easured using a Xenogen imager (Xenogen). At the experimental endpoint, animals were euthanized, and tumors were removed and weighed. Tumor surface area was assessed using a caliper; tumor length and width were measured in centimeters, and the product was taken to determine surface area.

Sequence Alignment

The miR-125b seed region and IRF4 39 UTR sequences from human (Homo sapien), mouse (Mus musculus), cat (Felis catus), and armadillo (Dasypus novemcinctus) were obtained and aligned using Targetscan program.

Luciferase Reporter Assay 293T cells were cotransfected with pcDNA-125b or pcDNA, as well as a β-gal expression vector, and the pMIR-REPORT vectors containing 39 UTRs of Cut11, Picalm, IRF4, or 2-mer. The luciferase activity was quantified 48 hours later and normalized to β-gal activity as described in O'Connell et al., Proc. Natl. Acad. Sci. USA, 106:7113-7118 (2009); Rao et al., Immunity 33:48-59 (2010).

RNA Preparation and Quantification

RNA was isolated using TRIzol (Invitrogen), RNEasy (Qiagen), or miRNEasy (Qiagen). Quantitative real-time PCR (qPCR) was conducted using a 7300 Real-time PCR machine (Applied Biosystems) or a Realplex Real-time PCR machine (Eppendorf). SYBR Green was used to assay IRF4 and L32 expression. PCR with primer sequences for mouse pri-miR-125b-1 and pri-miR-125b-2 (described in Zhou et al., Nucleic Acids Res., 38:3222-3232 (2010)) were used to assay levels of miR-125b primary transcripts. TaqMan-based qPCR was conducted to assay miR-125b, miR-125a, and snoRNA-202 (Applied Biosystems). Primer sequences are listed in Table I.

Example 1

Enriched Expression of miR-125b in Macrophages

Figure 2:
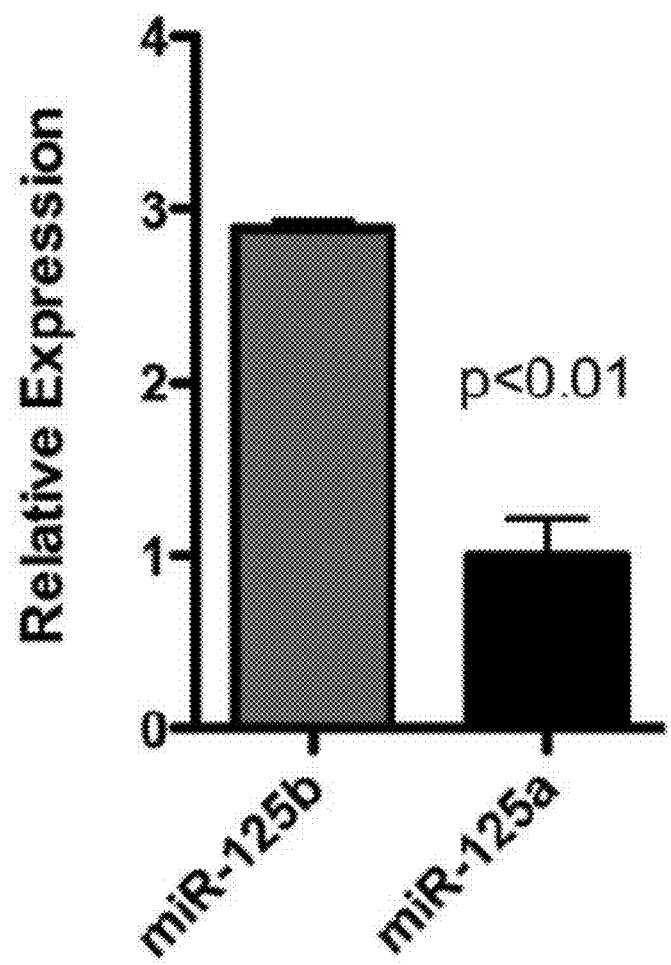
FIG. 2 shows relative expression of miR-125b and miR-125a in peritoneal macrophages. Data represents the mean and SEM of three biological replicates.

To investigate the expression of miR-125b in different immune cells and tissues, RNA was harvested from total splenocytes, thymocytes, splenic T cells, splenic B cells, and peritoneal macrophages from C57BL/6 mice. Levels of miR-125b were assessed by reverse transcription followed by quantitative PCR. As shown in FIG. 1A, the expression of miR-125b was much higher in macrophages compared with the other immune cells and tissues. Also shown in FIG. 2, within macrophages, miR-125b levels were significantly higher than its homolog, miR-125a, indicating that miR-125b is the dominant isoform in these cells.

RT-PCR was performed for each of the two primary transcripts of miR-125b. As shown in FIG. 1B, macrophages express primarily miR-125b-1 (FIG. 1B).

Example 2

Enforced Expression of miR-125b Enhances Macrophage Activation Status

Figure 3:
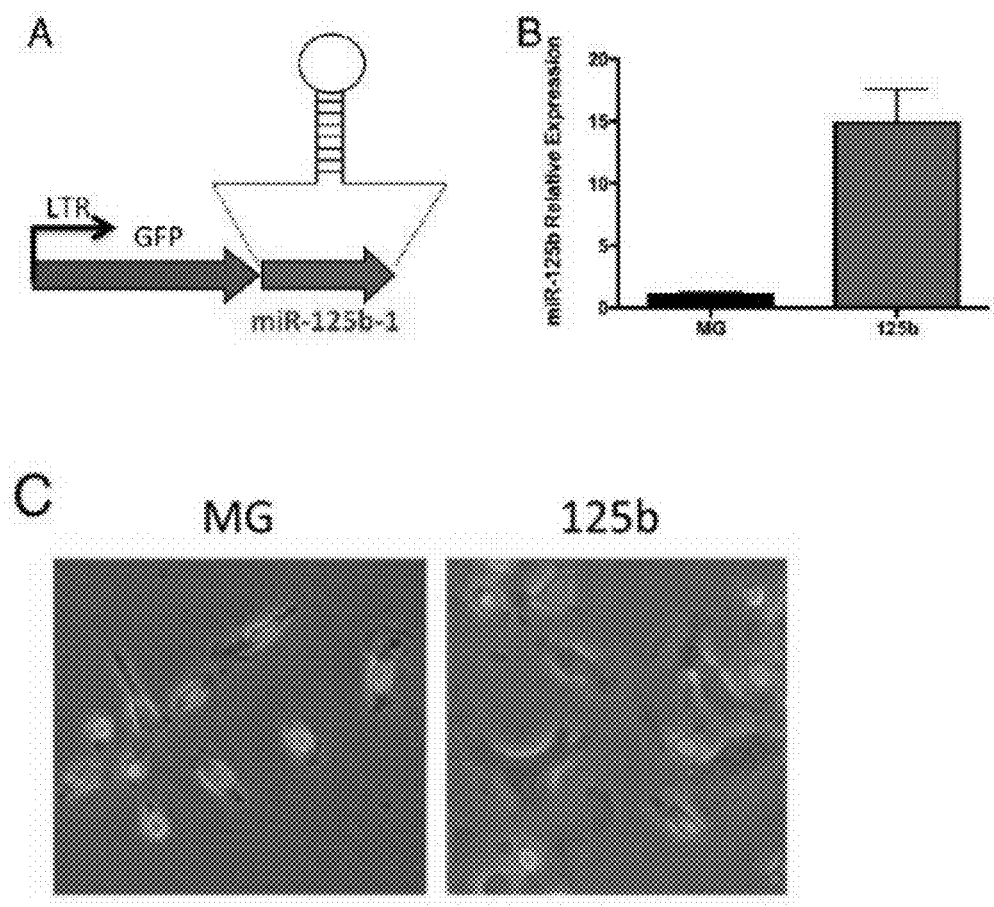
FIG. 3 shows miR-125b enhances basal macrophage activation.
Figure 3:
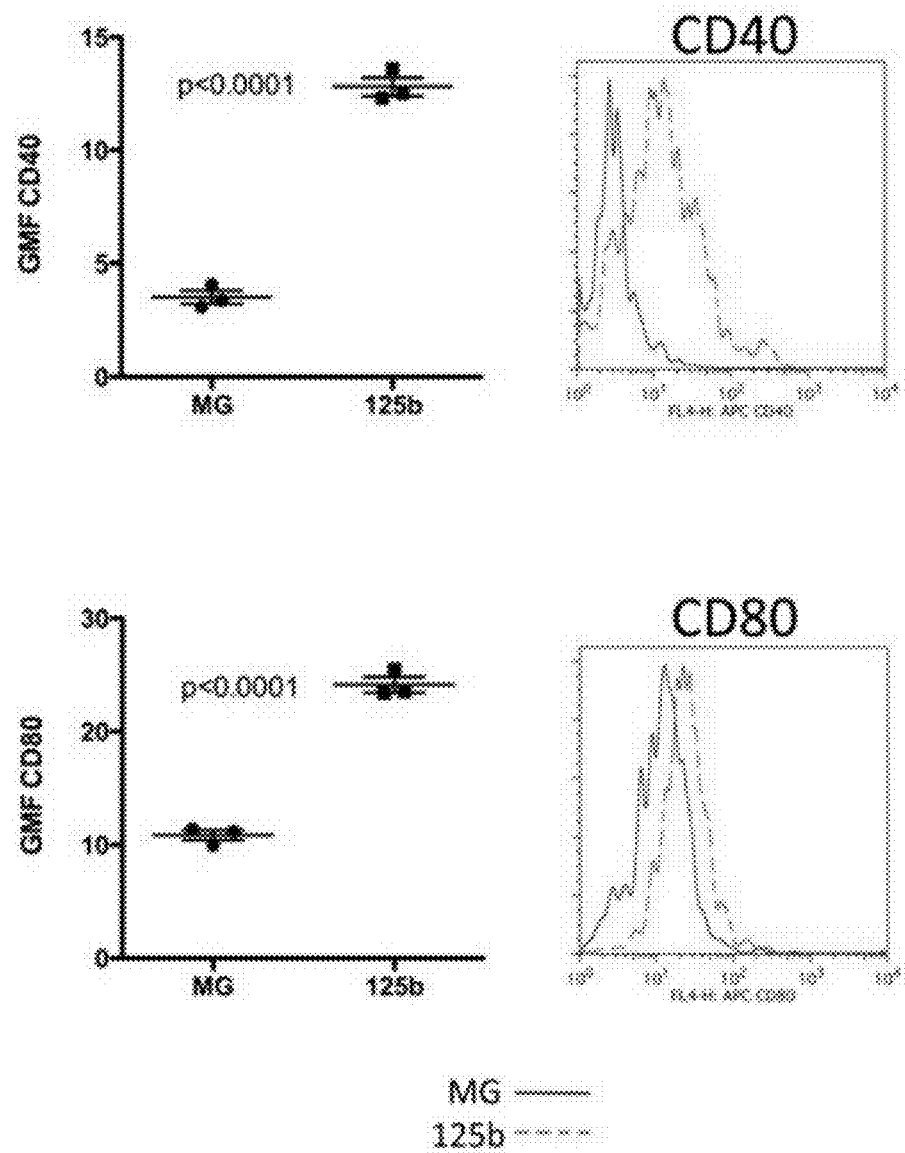

To examine the response of macrophages to miR-125b, a miR-125b1 overexpression system based on the MG vector (MG-miR-125b) and originally derived from the murine stem cell virus was used (FIG. 3A). Bone marrow cells isolated from C57BL/6 mice were spin-infected with either MG-miR-125b or MG control vector. These cells were then differentiated into BMMs by treatment with M-CSF. Using this system, miR-125b1 was overexpressed 15-fold above endogenous levels in BMMs (FIG. 3B).

As shown in FIG. 3C, miR-125b1-overexpressing BMMs acquired a spread morphology with extensive pseudopods that resembled activated macrophages. Flow cytometric analyses were performed. As shown in FIGS. 3D-E, expression of MHC II and the costimulatory molecules CD40, CD86, and CD80 is increased in these macrophages, indicating that these cells were indeed more activated. Ectopic expression of miR-125b1 in RAW264.7 macrophages gave similar results (FIG. 4), further reaffirming that miR-125b promotes activation of macrophages.

Example 3 miR-125b Increases Macrophage Response to IFN-γ

Figure 4:
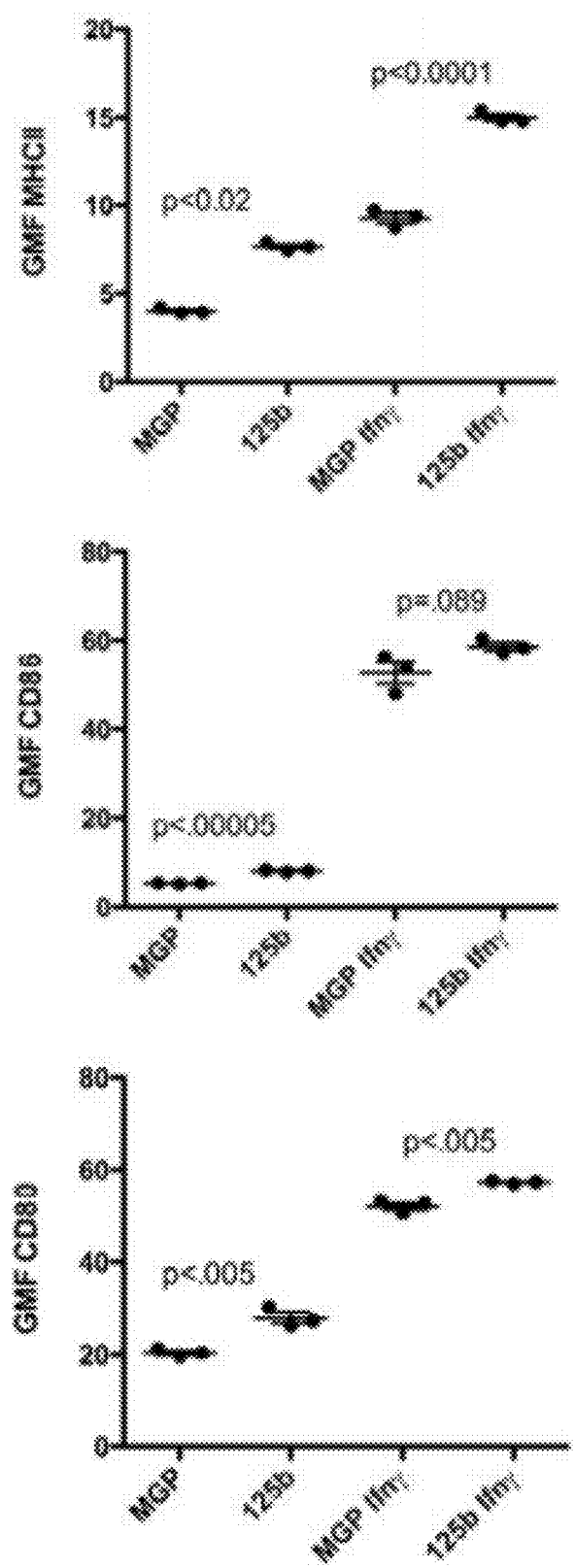
FIG. 4 shows surface expression of the activation markers MHCII, CD86 and CD80 in media and IFNγ treated RAW264.7 macrophages. All data shown is the mean with SEM of three samples per group, and is representative of two independent experiments.
Figure 5A:
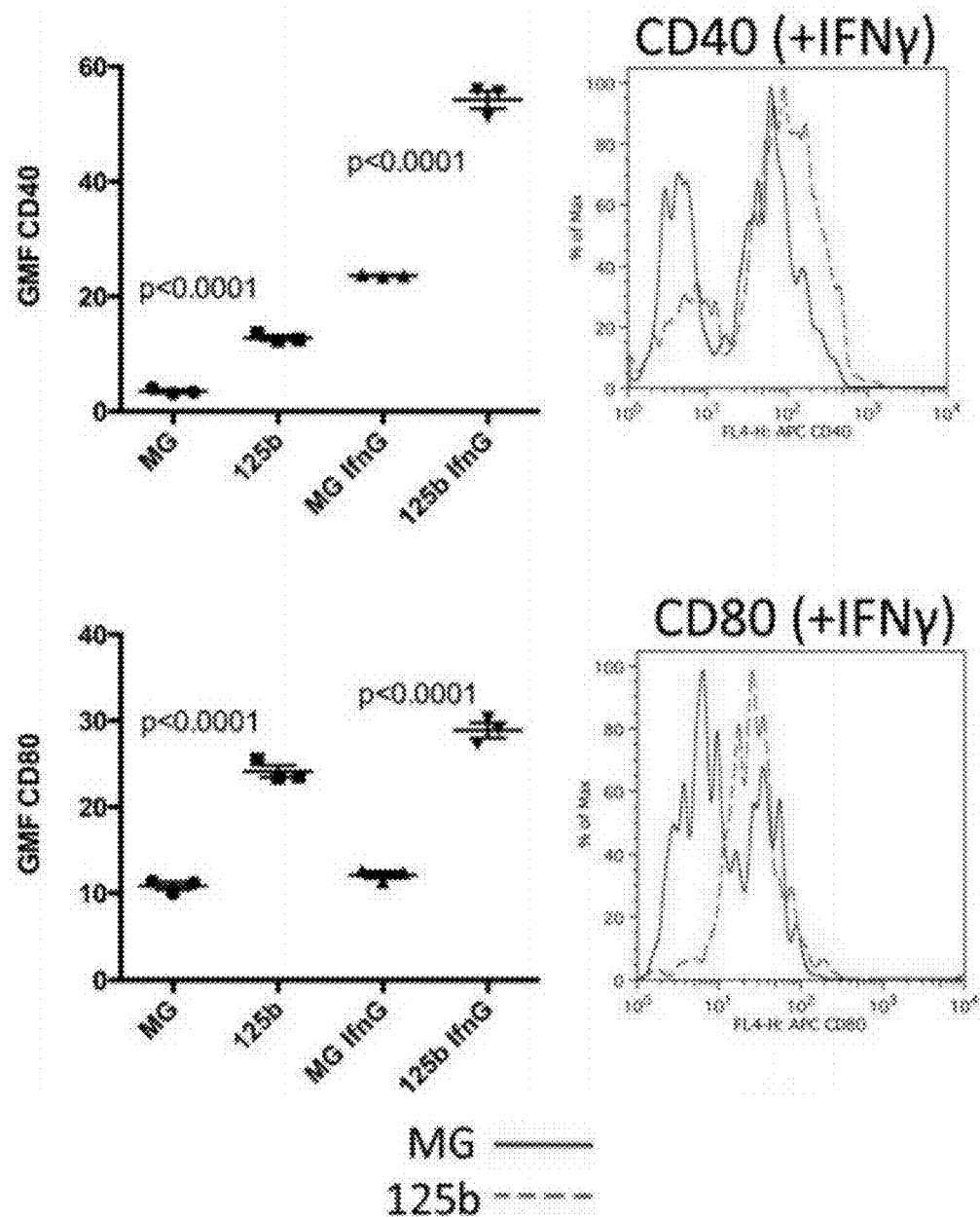
FIG. 5A shows surface expression of MHC II, CD40, CD86, and CD80 in response to media alone or IFN-γ. A representative flow cytometric plot of the IFN-g-treated samples is shown for each factor.

Effect of miR-125b on the responsiveness of macrophages was assessed by stimulating these cells with IFN-γ. As shown in FIG. 5A, IFN-γ treatment increased the expression of MHC II, CD40, CD86, and CD80 activation markers in control macrophages, whereas miR-125b1-overexpres sing macrophages expressed significantly higher levels of these markers. Similar results were obtained in RAW264.7 macrophages with enforced miR-125b expression (FIG. 4).

Figure 5B:
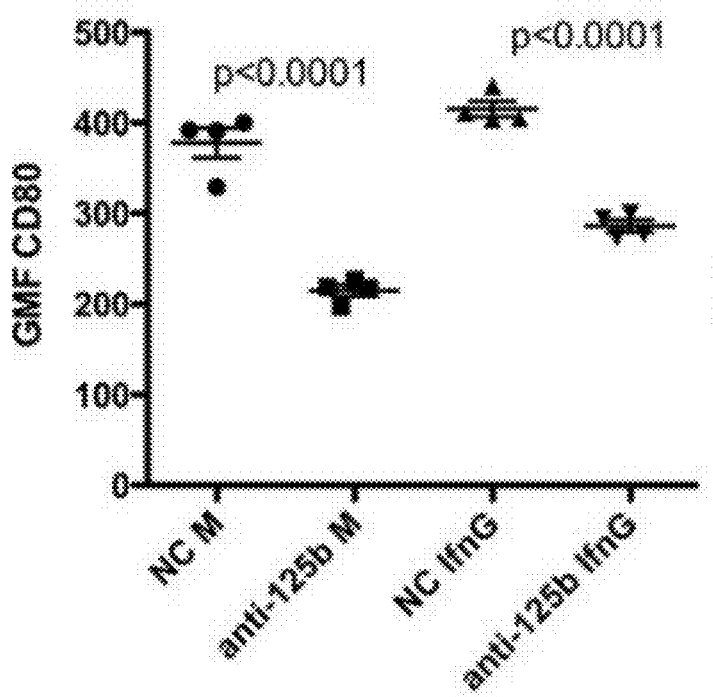
FIG. 5B Raw264.7 macrophages electroporated with negative control (NC) or anti-miR-125b (a125b) were subjected to flow cytometry for the surface expression of CD80. A representative FACS plot of the media-treated samples is shown.
Figure 5B:
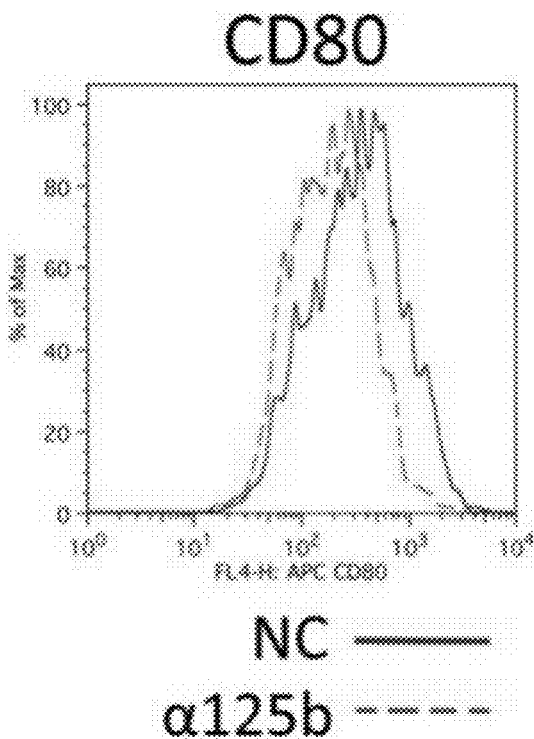

To examine whether reducing the concentration of miR-125b had an effect inverse to that of overexpression, RAW264.7 macrophages were treated with synthetic antisense oligonucleotides (anti-miR5), and surface CD80 levels were monitored as an indication of the cells' activation status. As shown in FIG. 5B, anti-miR-125b caused a reduction of both basal and IFN-g-induced levels of CD80 compared with cells treated with a control anti-miRNA. The data indicate that miR-125b controls CD80 expression in macrophages under normal, physiological conditions.

Figure 5C:
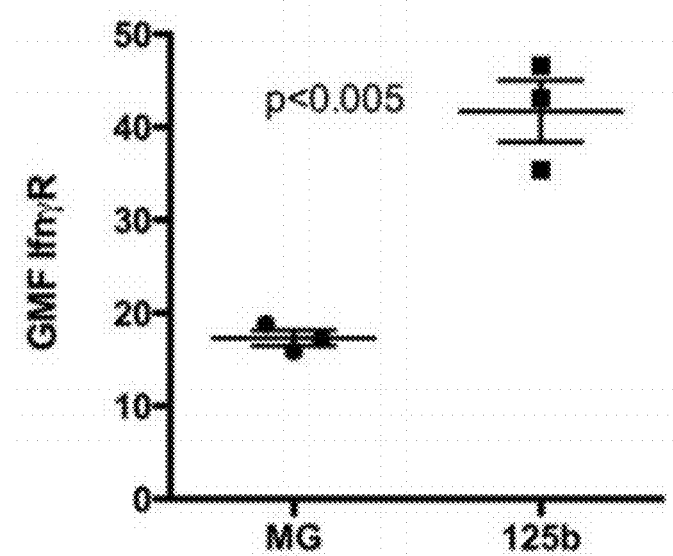
FIG. 5C shows surface expression of IFN-γR in control (MG) versus miR-125b-overexpressing macrophages. A representative FACS plot is shown. All data shown represent the mean expressed with SEM of three samples per group and are representative of two independent experiments.
Figure 5C:
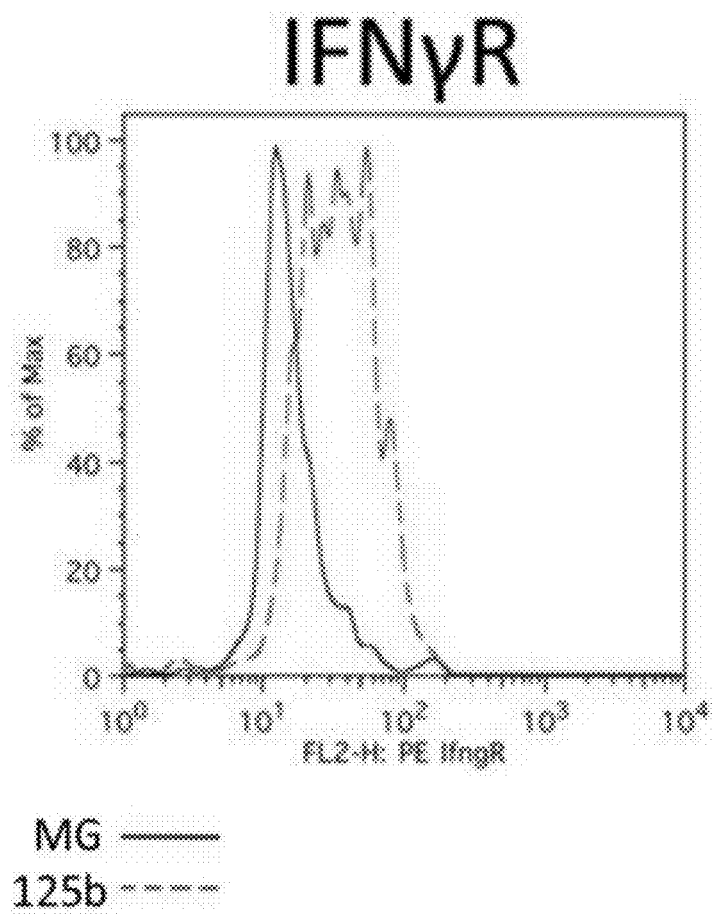
Figure 6:
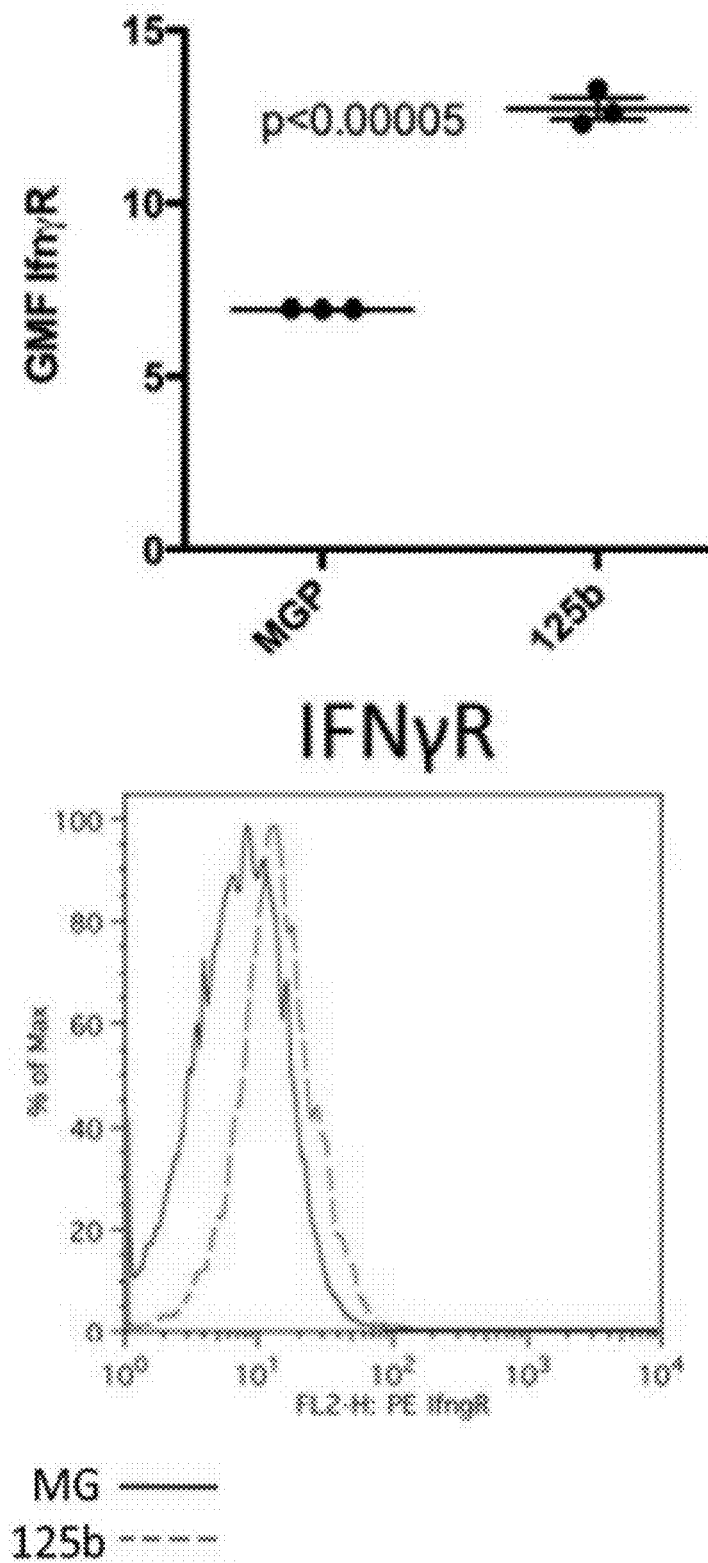
FIG. 6 shows that surface expression of IFNγR in MGP control or miR-125b over-expressing RAW264.7 macrophages. All data shown is the mean with SEM of three samples per group, and is representative of two independent experiments.

To investigate whether increased expression of the IFNγR causes the heightened response to IFN-γ in miR-125b-treated cells, levels of surface IFN-γR were measures. As shown in FIGS. 5C and 6, miR-125b-overexpressing BMMs and RAW264.7 macrophages expressed significantly higher levels of surface IFN-γR. Therefore, in addition to potentiating macrophage activation, miR-125b promotes enhanced macrophage responsiveness to IFN-γ and increases surface expression of its cognate receptor.

Example 4 miR-125b Enhances Macrophage-Mediated Function

Figure 7:
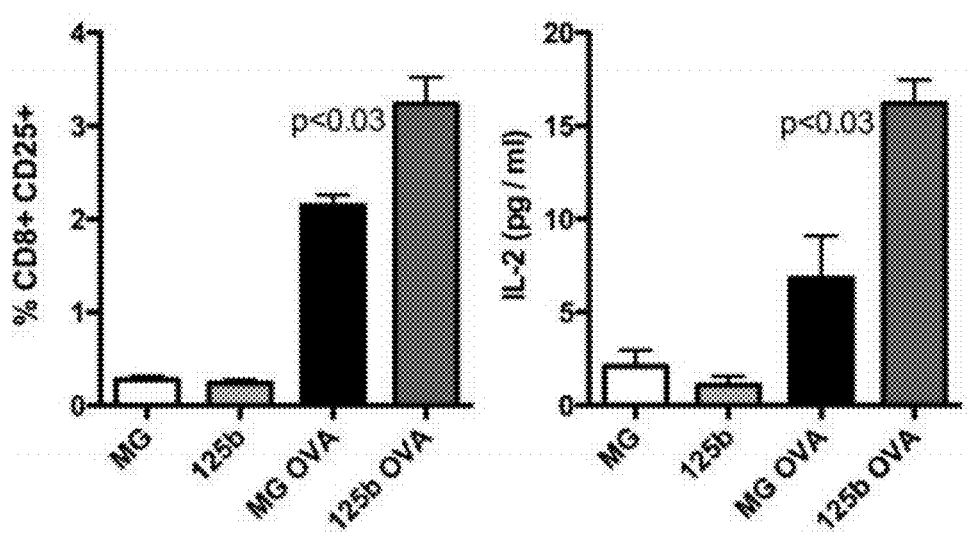
FIG. 7 shows that miR-125b enhances macrophage function.
Figure 7:
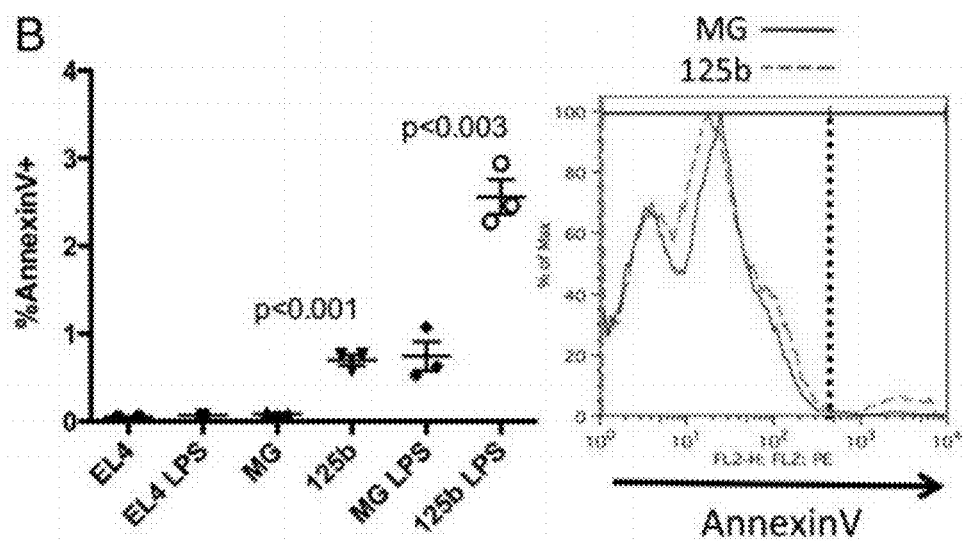
Figure 7:
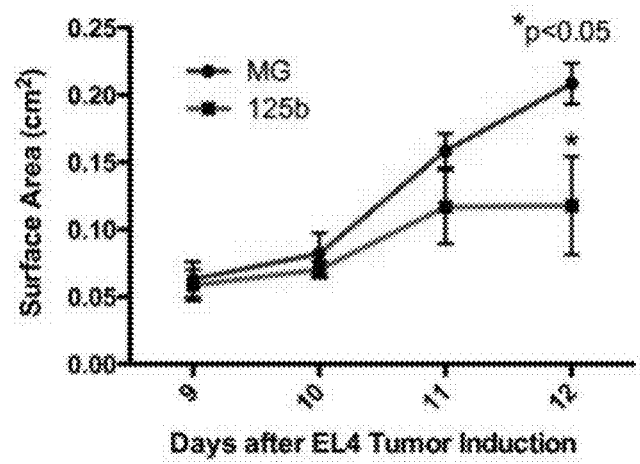
Figure 7:
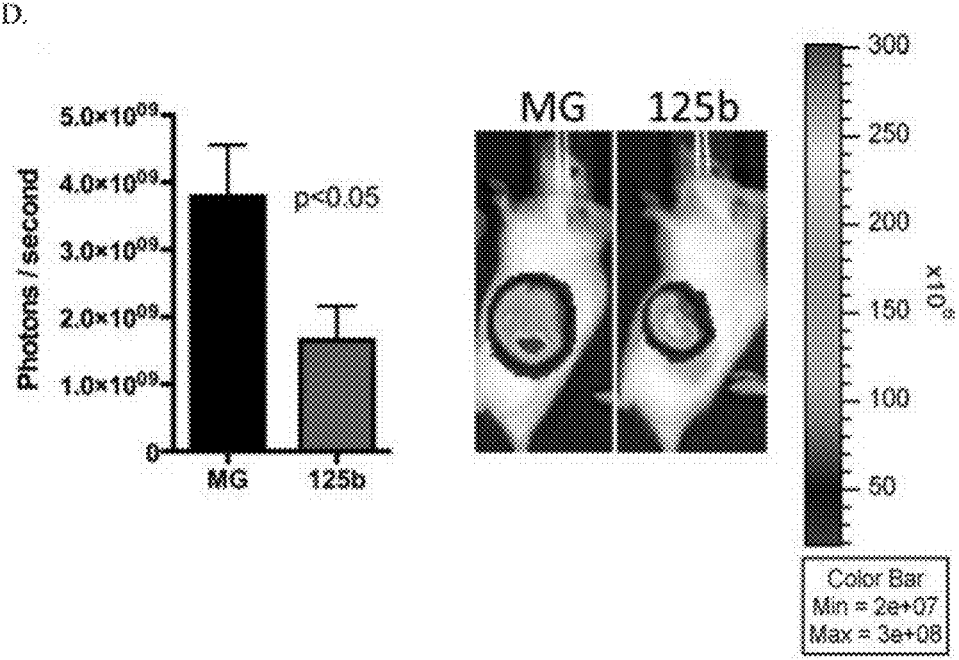
Figure 7:
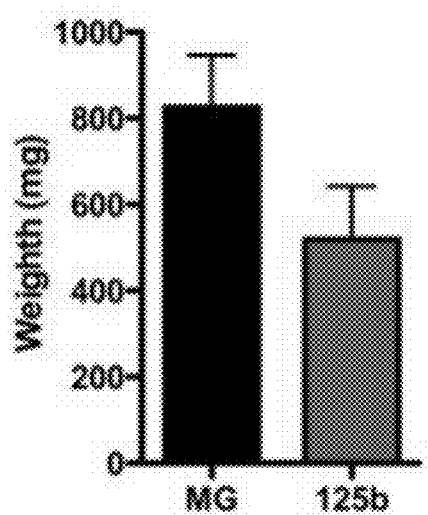

Because miR-125b drove macrophages to adopt an elevated activation status and become more responsive to stimulatory cues, the question whether miR-125b also potentiate macrophage-mediated immune function was examined, for example, whether miR-125b increases the ability of macrophages to present antigens and induce activation of T cells was investigated.

miR-125b1-overexpres sing macrophages were co-cultured with transgenic T cells that express a chicken OVA-specific TCR (OT1) in the presence of OVA. Indeed, compared with control macrophages, miR-125b-overexpressing cells were more effective at inducing T cell activation, which was indicated by increased CD25 expression and IL-2 secretion by the T cells in response to OVA (FIG. 7A). Therefore, enforced expression of miR-125b led to an elevated ability of macrophages to act as effective APC for stimulation of T cell responses.

In addition to serving as antigen-presenting cell (APC), another major function of macrophages is to eliminate aberrant cells, such as tumor cells. The effectiveness of miR-125b-stimulated macrophages in killing tumor cells was assessed. EL4-Fluc thymoma tumor line, which was engineered to express luciferase, was used and co-cultured with either control macrophages or macrophages overexpres sing miR-125b. Consistent with augmented function, miR-125b-expressing macrophages were better at inducing apoptosis of EL4-Fluc cells (FIG. 7B). Macrophages exposed to LPS gained the ability to induce apoptosis of EL4-Fluc cells, with miR-125b-overexpressing macrophages having superior effectiveness (FIG. 7B).

To test whether miR-125b levels in macrophages affect tumor killing in vivo, mice was s.c. co-injected with equal numbers of LPS-activated control or LPS-activated miR-125b1-overexpressing macrophages with EL4-Fluc cells. The growth of the resulting tumor in the mice was tracked by measuring tumor surface area over time. Because EL4-Fluc cells were engineered to express luciferase, monitored tumor growth was also monitored by measuring luminescence in vivo. As shown in FIG. 7C, consistent with the in vitro data, macrophages with miR-125b ectopic expression suppressed the ability of EL4 cells to expand in vivo. At the endpoint of the experiment on day 12, animals injected with MG-125b1 macrophages had smaller EL4-derived tumors that were significantly less luminescent than those injected with control macrophages (FIGS. 7D-E). Therefore, this example illustrates that miR-125b expression in macrophages aids macrophages in preventing the expansion of tumorigenic cells, further demonstrating that miR-125b enhances macrophage function.

Example 5

IRF4 is a miR-125b Target in Macrophages

This example illustrates IRF4 is a primary target of miR-125b in regulating macrophage activation.

Figure 8:
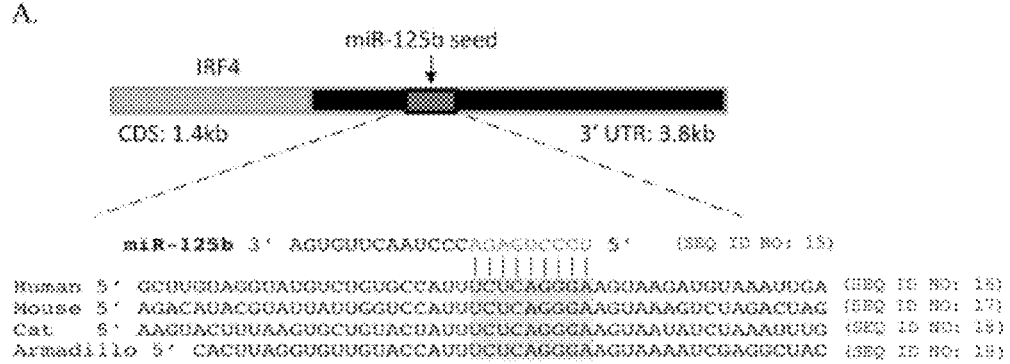
FIG. 8 shows that IRF4 is a target of miR-125b in macrophages.
Figure 8:
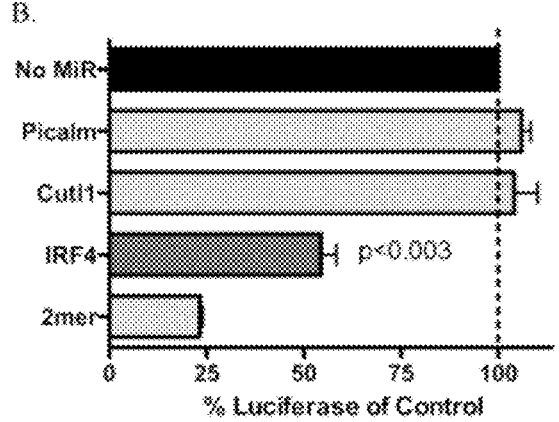
Figure 8:
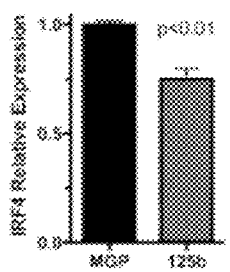
Figure 8:
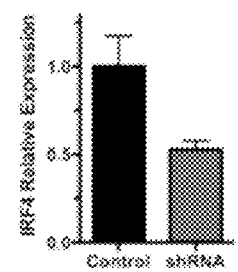
Figure 8:
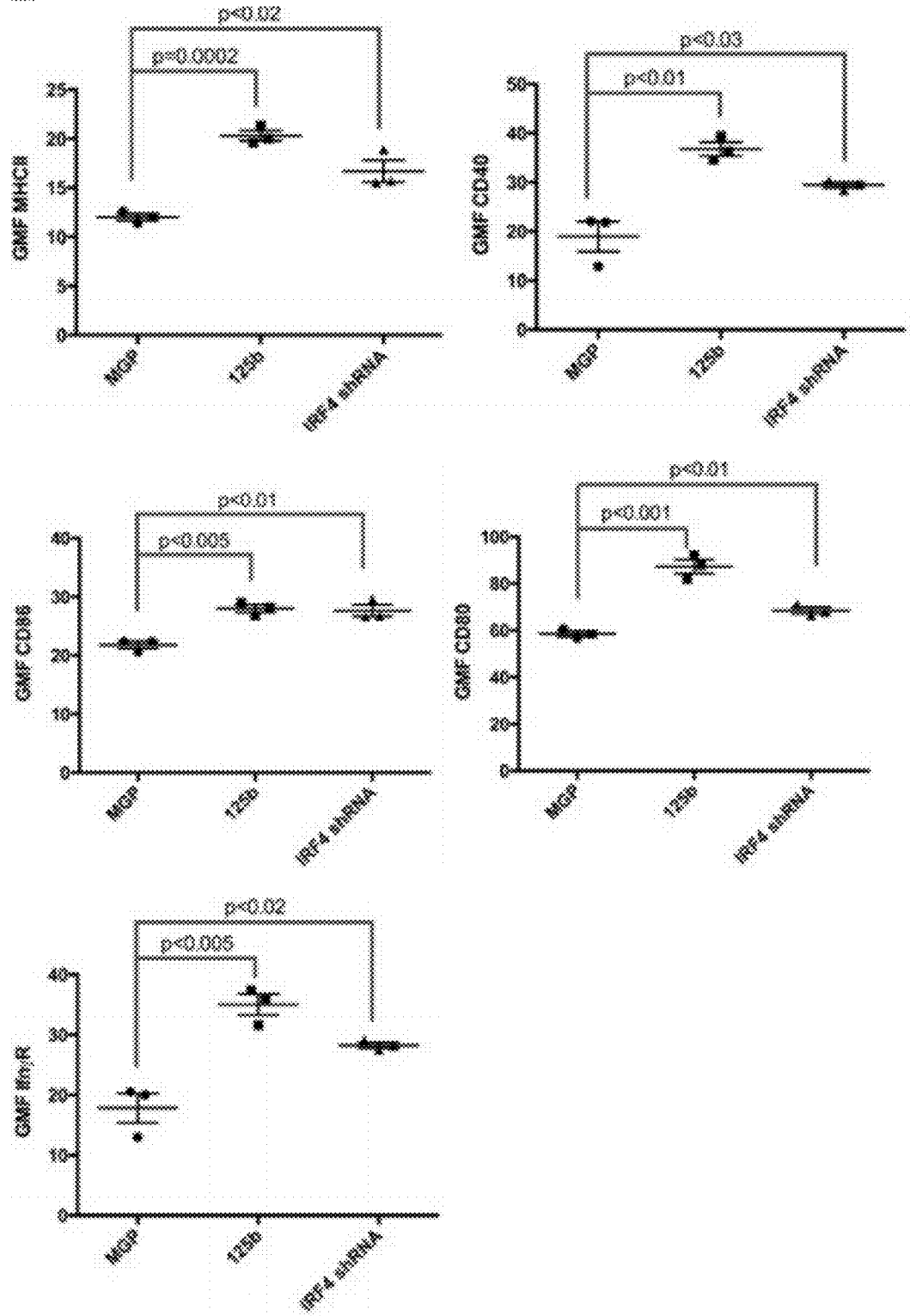

To identify targets regulated by miR-125b that modulate macrophage activation, TargetScan 5.1 was used to identify transcripts in the mouse genome that contain conserved putative miR-125b binding sites in their 39 UTRs. Among these genes, the 39 UTR of IRF4 harbored a conserved miR-125b binding site (FIG. 8A) and had been previously validated as a miR-125b target in B cell lines. As shown in FIGS. 8B and 8C respectively, miR-125b indeed represses via the 39 UTR of IRF4 and miR-125b inhibits IRF4 expression in macrophages.

Using the MGP retroviral vector system described in O'Connell et al., Proc. Natl. Acad. Sci. USA, 106:7113-7118 (2009), the expression of IRF4 was knocked down using RNA interference (FIG. 8D) and its effect in macrophages was examined. MGP-125b1 led to a 6-fold increase in miR-125b in BMMs. Similar to miR-125b overexpression, decreased IRF4 expression resulted in increased surface expression of MHC 11, CD40, CD86, CD80, and IFN-γR (FIG. 8E). Therefore, IRF4 knockdown in macrophages enhances activation, mimicking the miR-125b overexpression phenotype. These data further demonstrate that IRF4 is a negative regulator of macrophage proinflammatory pathways.

Example 6

Treatment of Tumor

This example illustrates the treatment of a patient suffering from or at risk of developing thymoma.

A patient suffering from or at risk of developing thymoma is identified and administered an effective amount of an miR-125b oligonucleotide. The miR-125b oligonucleotide is administered to the patient by contacting macrophages of the patient with an expression construct containing a nucleic acid encoding the miR-125b oligonucleotide. The expression construct express the miR-125b oligonucleotide in the macrophages, thereby increasing the induction of apoptosis of thymoma tumor cells in the patient. The appropriate dosage (i.e., the expression level of the miR-125 oligonucleotide from the expression construct) and treatment regimen can be readily determined by skilled artisans based on a number of factors including, but not limited to, the route of administration and the patient's disease state. The treatment efficacy is evaluated by observing delay or slowing of disease progression, amelioration or palliation of the disease state, and remission.

Example 7

Treatment of Multiple Sclerosis

This example illustrates the treatment of a patient suffering from or at risk of developing Multiple Sclerosis.

A patient suffering from or at risk of developing Multiple Sclerosis is identified and administered an effective amount of an antisense miR-125b oligonucleotide. The antisense miR-125b oligonucleotide is administered to the patient by contacting macrophages of the patient with an expression construct containing a nucleic acid encoding the antisense miR-125b oligonucleotide. The expression construct express the antisense miR-125b oligonucleotide in the macrophages, thereby inhibiting proliferation of myeloid cells in the patient. The appropriate dosage (i.e., the expression level of the antisense miR-125b oligonucleotide from the expression construct) and treatment regimen can be readily determined by skilled artisans based on a number of factors including, but not limited to, the route of administration and the patient's disease state. The treatment efficacy is evaluated by observing delay or slowing of disease progression, amelioration or palliation of the disease state, and remission.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases at least one and one or more to introduce claim recitations. However, the use of such phrases should not be construed to imply that the introduction of a claim recitation by the indefinite articles "a" or an limits any particular claim containing such introduced claim recitation to embodiments containing only one such recitation, even when the same claim includes the introductory phrases one or more or at least one and indefinite articles such as "a" or an (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for activating macrophages in a mammal, comprising
identifying a mammal in need of macrophage activation;
administering a microRNA-125b (miR-125b) oligonucleotide to macrophages in the mammal; and
measuring macrophage activation in the mammal.

2. The method of claim 1, wherein the miR-125b oligonucleotide is selected from the group consisting of a mature miR-125b1 oligonucleotide, a mature miR-125b2 oligonucleotide, a pre-miR-125b1 oligonucleotide, a pre-miR-125b2 oligonucleotide, and a miR-125 seed sequence.

3. The method of claim 1, wherein the miR-125b oligonucleotide comprises a nucleic acid sequence selected from the group consisting of SEQ ID NOs: 1-7 and 31.

4. The method of claim 1, wherein the administering the miR-125b oligonucleotide to the macrophages comprises contacting the macrophages with an expression construct comprising a nucleic acid encoding the miR-125b oligonucleotide, thereby the miR-125b is expressed in the macrophage.

5. The method of claim 1, wherein the activation of the macrophages comprises T cell activation or inhibiting IRF4 expression in the macrophages.

6. The method of claim 1, wherein the activation of macrophages comprises increasing IFN-γ response of the macrophages in the mammal.

7. The method of claim 6, wherein the increasing IFN-γ response of the macrophages comprises increasing surface expression of IFN-γ receptor (IFN-γR) on the macrophages.

8. The method of claim 1, wherein the activation of macrophages comprises increasing surface expression of one or more activation markers of the macrophages in the mammal.

9. The method of claim 8, wherein the one or more activation markers are selected from MHC II, CD40, CD86, CD80, or any combination thereof.

10. The method of claim 1, wherein the macrophages are selected from the group consisting of alveolar macrophages, histiocytes, kupffer cells microglia, epithelioid cells, osteoclasts, sinusoidal lining cells, giant cells, peritoneal macrophages, tumor associated macrophages (TAM), and a combination thereof.

11. The method of claim 10, wherein the macrophages are peritoneal macrophages, TAM, or a combination thereof.

12. The method of claim 1, wherein the mammal suffers from chronic infection or cancer.

13. The method of claim 12, wherein the cancer is solid tumor.

14. The method of claim 1, wherein the miR-125b oligonucleotide comprises a miR-125 seed sequence.

15. The method of claim 14, wherein the miR-125 seed sequence is SEQ ID NO: 4.

16. The method of claim 1, wherein the miR-125b oligonucleotide is a nucleic acid sequence selected from the group consisting of SEQ ID NOs: 1-7 and 31.

* * * * *